United States Patent
Li et al.

(10) Patent No.: US 11,576,608 B2
(45) Date of Patent: Feb. 14, 2023

(54) SYSTEMS AND METHODS FOR LYMPH NODE AND VESSEL IMAGING

(71) Applicant: Massachusetts Institute of Technology, Cambridge, MA (US)

(72) Inventors: Zhongming Li, Cambridge, MA (US); Angela Belcher, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 498 days.

(21) Appl. No.: 16/781,338

(22) Filed: Feb. 4, 2020

(65) Prior Publication Data

US 2020/0245921 A1  Aug. 6, 2020

Related U.S. Application Data

(60) Provisional application No. 62/848,178, filed on May 15, 2019, provisional application No. 62/800,674, filed on Feb. 4, 2019.

(51) Int. Cl.
| | |
|---|---|
| *G06K 9/00* | (2022.01) |
| *A61B 5/00* | (2006.01) |
| *G01N 21/21* | (2006.01) |
| *G01N 21/35* | (2014.01) |

(Continued)

(52) U.S. Cl.
CPC ............ *A61B 5/418* (2013.01); *A61B 5/0062* (2013.01); *A61B 5/0082* (2013.01); *G01N 21/21* (2013.01); *G01N 21/35* (2013.01); *G06T 7/0012* (2013.01); *G01N 2021/3137* (2013.01); *G06T 2207/30004* (2013.01)

(58) Field of Classification Search
CPC ..... A61B 5/418; A61B 5/0062; A61B 5/0082; A61B 5/004; A61B 2562/0233; A61B 5/415; A61B 5/0059; G01N 21/35; G01N 2021/3137; G06T 7/0012; G06T 2207/30004

See application file for complete search history.

(56) References Cited

U.S. PATENT DOCUMENTS

| | | |
|---|---|---|
| 6,640,130 B1 | 10/2003 | Freeman |
| 9,204,805 B2 | 12/2015 | Panasyuk |
| 9,795,303 B2 | 10/2017 | Panasyuk |

(Continued)

FOREIGN PATENT DOCUMENTS

CN    104586361 A    5/2015

OTHER PUBLICATIONS

Akagi, Y., et al. "Lymph node evaluation and survival in colorectal cancer: review of population-based, prospective studies." Anticancer research 33.7 (2013): 2839-2847.

(Continued)

*Primary Examiner* — Tom Y Lu
(74) *Attorney, Agent, or Firm* — Quarles & Brady LLP

(57) ABSTRACT

This disclosure provides a method for imaging lymph nodes and lymphatic vessels without a contrast agent. The method includes providing, using an optical source, an infrared illumination to a region of a subject having at least one lymphatic component, detecting a reflected portion of the infrared illumination directly reflected from the region using a sensor positioned thereabout, and generating at least one image indicative of the at least one lymphatic component in the subject using the reflected portion of the infrared illumination.

51 Claims, 13 Drawing Sheets

(51) Int. Cl.
G06T 7/00 (2017.01)
G01N 21/31 (2006.01)

(56) References Cited

U.S. PATENT DOCUMENTS

| | | | |
|---|---|---|---|
| 9,968,285 B2 | 5/2018 | Valsan | |
| 10,231,626 B2* | 3/2019 | Steinbach | A61B 5/0071 |
| 10,849,710 B2* | 12/2020 | Liu | A61B 90/20 |
| 11,039,090 B2* | 6/2021 | Liu | H04N 5/332 |
| 2006/0058683 A1* | 3/2006 | Chance | A61B 5/6834 |
| | | | 600/407 |
| 2018/0270474 A1* | 9/2018 | Liu | A61B 6/508 |

OTHER PUBLICATIONS

Amri, R., et al. "The prognostic value of lymph node ratio in colon cancer is independent of resection length." The American Journal of Surgery 212.2 (2016): 251-257.
Bairati, A. et al. Studies On The Ultrastructure Of The Lymph Nodes I, ?Zeitschrift für Zellforsehung 63, 644-672 (1964).
Benvenuto-Andrade, C., et al. "Differences between polarized light dermoscopy and immersion contact dermoscopy for the evaluation of skin lesions." Archives of dermatology 143.3 (2007): 329-338.
Boppart SA et al. ("Label-free optical imaging technologies for rapid translation and use during intraoperative surgical and tumor margin assessment," J Biomed Opt. 23(2):021104, Feb. 2018).
Cheraghlou, S., et al. "Prognostic value of lymph node yield and density in head and neck malignancies." Otolaryngology—Head and Neck Surgery 158.6 (2018): 1016-1023.
Del Paggio, J. C., et al. "Lymph node evaluation for colon cancer in routine clinical practice: a population-based study." Current Oncology 24.1 (2017): e35.
Divi, V., et al. "Lymph node count from neck dissection predicts mortality in head and neck cancer." Journal of Clinical Oncology 34.32 (2016): 3892-3897.
Groner, W, et al. "Orthogonal polarization spectral imaging: a new method for study of the microcirculation." Nature medicine 5.10 (1999): 1209-1212.
Gutierrez, J. C., et al. "How many lymph nodes properly stage a periampullary malignancy?." Journal of Gastrointestinal Surgery 12.1 (2008): 77-85.
Herranz M et al. ("Optical Imaging in Breast Cancer Diagnosis: The Next Evolution," J. of Onc., 863747, 2012).
Hong, G., et al. "Through-skull fluorescence imaging of the brain in a new near-infrared window." Nature photonics 8.9 (2014): 723.
Lee, E.S. et al. ("Current Status of Optical Imaging for Evaluating Lymph Nodes and Lymphatic System," Kor. J. Rad. 16(1):21-31, Jan. 2015).

Lee, M. C., et al. "Factors affecting lymph node yield in patients undergoing axillary node dissection for primary breast cancer: a single-institution review." Annals of surgical oncology 19.6 (2012): 1818-1824.
Liao, S., et al. "Method for the quantitative measurement of collecting lymphatic vessel contraction in mice." Journal of biological methods 1.2 (2014).
Lykke, J., et al. "Lymph node yield and tumour subsite are associated with survival in stage I-III colon cancer: results from a national cohort study." World journal of surgical oncology 17.1 (2019): 62.
Munn, LL et al. "Imaging the lymphatic system." Microvascular research 96 (2014): 55-63.
Rieger, N. A., et al. "Quality of pathology reporting impacts on lymph node yield in colon cancer." Journal of Clinical Oncology 25.4 (2007): 463-463.
Schoenleber, S. J., et al. "Factors influencing lymph node recovery from the operative specimen after gastrectomy for gastric adenocarcinoma." Journal of Gastrointestinal Surgery 13.7 (2009): 1233-1237.
Sierzega, M., et al. "Factors predicting adequate lymph node yield in patients undergoing pancreatoduodenectomy for malignancy." World journal of surgical oncology 14.1 (2016): 248.
Thorn, C. C., et al. "What factors affect lymph node yield in surgery for rectal cancer?." Colorectal Disease 6.5 (2004): 356-361.
Tomlinson, J. S., et al. "Accuracy of staging node-negative pancreas cancer: a potential quality measure." Archives of surgery 142.8 (2007): 767-774.
Truesdale, M. D., et al. "Assessment of lymph node yield after pelvic lymph node dissection in men with prostate cancer: a comparison between robot-assisted radical prostatectomy and open radical prostatectomy in the modem era." Journal of endourology 24.7 (2010): 1055-1060.
Vakoc, B. J., et al. "Three-dimensional microscopy of the tumor microenvironment in vivo using optical frequency domain imaging." Nature medicine 15.10 (2009): 1219-1223.
Wilson, R. H., et al. "Review of short-wave infrared spectroscopy and imaging methods for biological tissue characterization." Journal of biomedical optics 20.3 (2015): 030901.
Wu, Z., et al. "Assessing the adequacy of lymph node yield for different tumor stages of colon cancer by nodal staging scores." BMC cancer 17.1 (2017): 498.
Yousefi S et al. ("Label-free optical imaging of lymphatic vessels within tissue beds in vivo," IEEE J Sel Top Quantum Electron, 20(2): 6800510, Mar. 2015).
Yousefi S et al. ("Label-free optical lymphangiography: development of an automatic segmentation method applied to optical coherence tomography to visualize lymphatic vessels using Hessian filters," J Biomed Opt, 18(8): 086004, Aug. 2013).

* cited by examiner

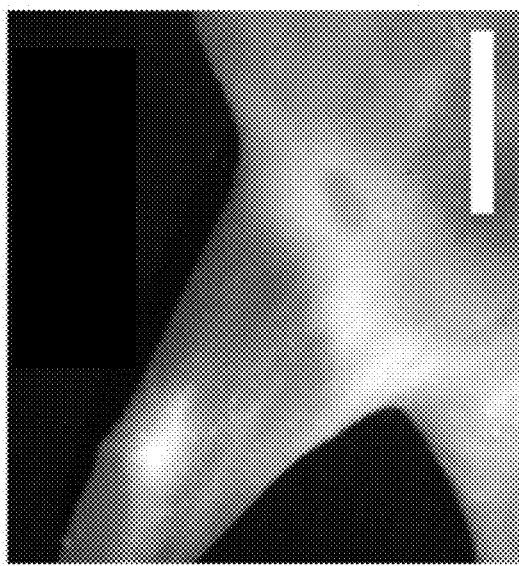
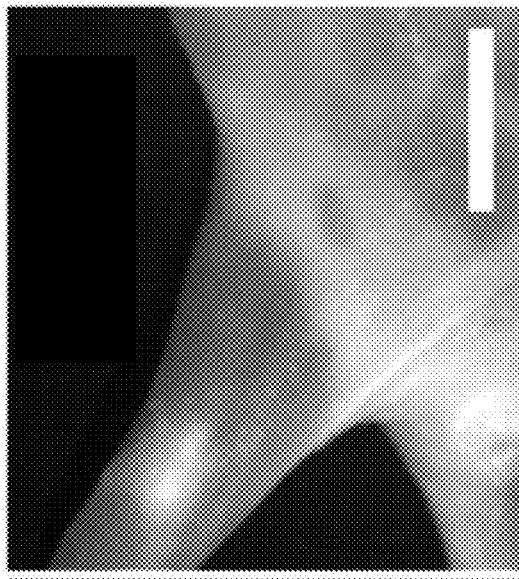
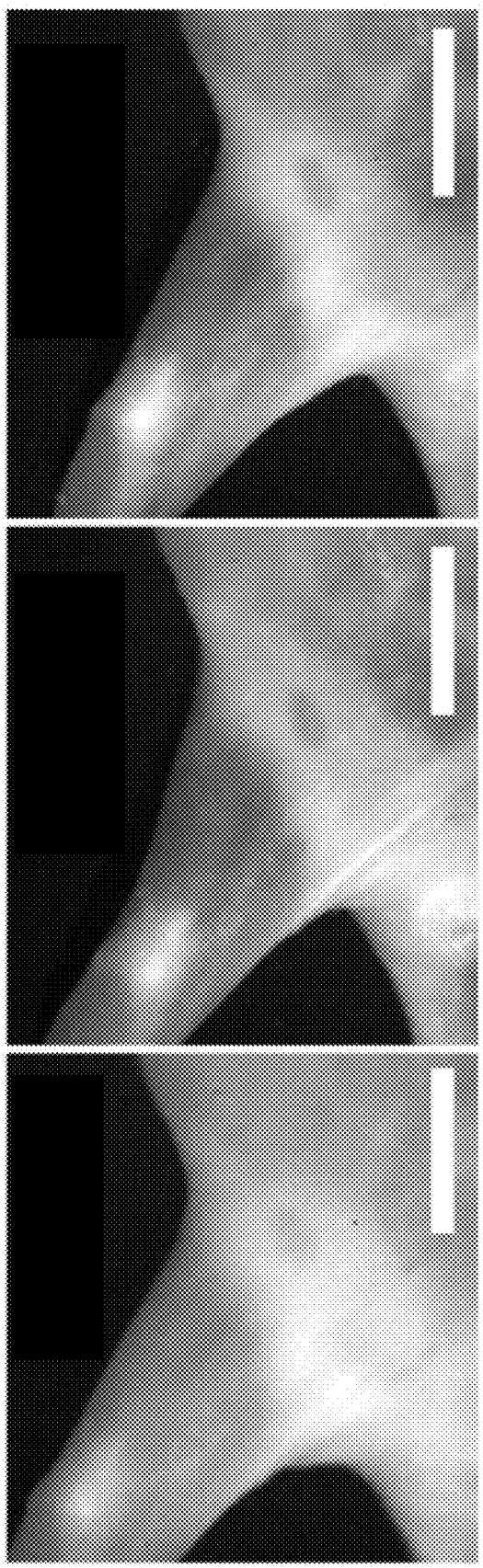
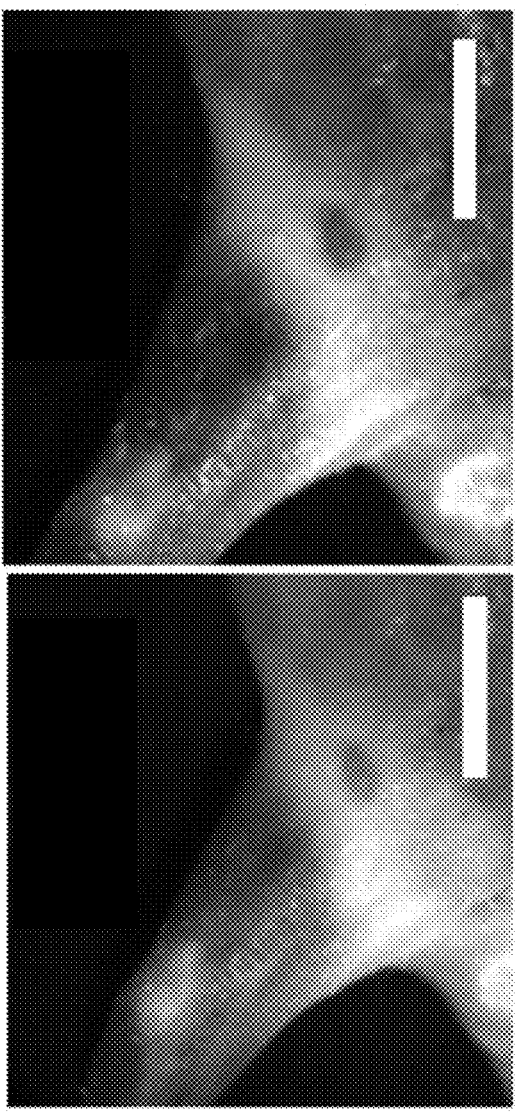

United States Patent

SYSTEMS AND METHODS FOR LYMPH NODE AND VESSEL IMAGING

CROSS-REFERENCE TO RELATED APPLICATIONS

This application is based on, claims the benefit of, and claims priority to U.S. Provisional Application No. 62/848,178, filed May 15, 2019, and to U.S. Provisional Application No. 62/800,674, filed Feb. 4, 2019, which are hereby incorporated by reference herein in their entirety for all purposes.

STATEMENT REGARDING FEDERALLY SPONSORED RESEARCH

This invention was made with government support under P30 CA014051 awarded by the National Institutes of Health. The government has certain rights in the invention.

BACKGROUND

Lymph nodes, also known as lymph glands, are oval-shaped organs that are widely present throughout the human and animal bodies. Lymph node is an integral part of the lymphatic system, which is responsible for the immune responses to protect the body from diseases and infections. The condition of lymph nodes can be directly indicative to one's health conditions. Swollen lymph nodes can be an indication of bacterial infection, virus infection, cancer, etc. Checking the condition of lymph nodes by imaging them is extremely useful to disease diagnosis, prevention, and treatment.

Currently, there are a number of imaging modalities to visualize and examine the lymph nodes. Traditionally, the standard method is lymphography. Lymphography involves injecting radiocontrast agents into patients and visualize the lymph nodes and lymphatic vessels with X-ray. This procedure is invasive, causes significant discomfort and involves using radioactive agents.

In recent years, cross sectional imaging modalities, including Computational Tomography (CT) and Magnetic Resonance Imaging (MRI), have become increasingly popular, in replacement of lymphography in lymph node visualization. Ultrasound and Positron Emission Tomography (PET) have also been demonstrated to be useful. Although with these techniques mentioned above, doctors are able to identify lymph nodes and make a reasonably accurate judgment of their conditions, they are general-purpose imaging modalities, so their working mechanisms are not designed to give the best contrast for lymph nodes specifically, unless specific contrasting agents are injected. As a result, other organs and tissues show up in these images with the same or sometimes even better contrast compared to lymph nodes, causing distractions to the task of finding and examining the lymph nodes. These general-purposed imaging modalities are not only not specific to lymph nodes, but also possess their own critical drawbacks. CT involves X-ray exposure and PET involves radioactive agents, which need to be carefully controlled in prevention of health hazards. MM requires expensive instrumentation and is not compatible with patients with metal implants. Ultrasound provides low imaging contrast and resolution mainly because of its long imaging wavelength.

Another common practice for lymph node imaging involves injecting dyes, either blue dyes or fluorescent dyes. The most common dye used for lymph node visualization is methylene blue, which is actually toxic. The dosage of this dye has to be carefully managed. Indocyanine green, a fluorescent dye, has also been used for lymph node imaging. Systems leveraging fluorescence dyes such indocyanine green and methylene blue include systems a FLARE™ system, a fluobeam system, SPY, FDPM, and a Photodynamic Eye system. Most of these use either a single image sensor (typically, a CCD) to capture visible (a reference image) and fluorescence images sequentially, or multiple cameras to image different spectra simultaneously or sequentially.

Dye based methods have numerous drawbacks. One drawback is that dyes can stimulate negative responses to some patients, especially people with kidney complications. Another drawback is that the dye injection method can be unreliable because of the leaky nature of the lymphatic system. Additionally, certain dye-based methods require invasive application of the dye.

For imaging systems that produce multiple images with the use of multiple cameras and/or sequential image acquisition, subsequent image registration is required. To properly coordinate differences in spatial parameters of the multiple images, such image processing must take into account changes in angular coordinate, potential relative motion between the system and the subject, or both. Other types of imagers include specialized CMOS sensors that can collect light via red-green-blue channel(s) (RGB) as well as a single channel in NIR-1.

There are some other reports in academic papers about using novel optical techniques to image lymph nodes, including optical speckle imaging, optical coherence tomography, etc. However, optical speckle imaging is highly susceptible to motion artifact, and optical coherence tomography involves sophisticated instrumentation and offers poor imaging contrast.

In summary, given the critical importance of lymph nodes to human health, there are no convenient and highly effective methods for visualizing lymph nodes. Cross sectional imaging methods are not convenient and not specific for visualization of lymph nodes unless contrasting agents are injected. Dye-based imaging techniques are generally highly invasive and incompatible with clinical settings like routine checks. A new imaging modality that is able to conveniently image lymph nodes with high specificity, high contrast without injecting any imaging contrasting agents will be a powerful tool for medical practitioners to examine the health of the patients, evaluate the effectiveness of a certain treatment, stage one's cancer condition, and so many other medical applications.

SUMMARY

The following is intended to give a brief summary of the disclosure and is not intended to limit the scope of the disclosure.

In one aspect, the present disclosure provides a system for imaging a lymphatic component. The system includes an optical source configured to provide infrared illumination having a polarization to a region of a subject having at least one lymphatic component, a sensor configured to sense a reflected portion of the infrared illumination having an opposite polarization to that of the polarization of illumination directly reflected from the region, and a controller in communication with the sensor. The controller is configured to receive, from the sensor, information corresponding to the reflected portion of the infrared illumination, generate at least one image indicative of the at least one lymphatic component in the subject using the information, and output the at least one image to at least one of a display and/or a memory.

In another aspect, the present disclosure provides a method for imaging lymph nodes or lymphatic vessels in vivo without a contrast agent. The method includes providing, using an optical source, an infrared illumination having a polarization to an in vivo region of a subject having lymph nodes or lymphatic vessels that are free of a contrast agent, detecting a reflected portion of the infrared illumination directly reflected from the region and having a opposite polarization to the polarization using a sensor positioned to receive the illumination directly reflected from the region, and generating at least one image indicative of the lymph nodes or lymphatic vessels that are free of a contrast agent in the subject using the reflected portion of the infrared illumination.

In yet another aspect, the present disclosure provides a method for imaging lymph nodes or lymphatic vessels without a mirror. The method includes providing, using an optical source, an infrared illumination to a region of a subject having lymph nodes or lymphatic vessels, detecting a reflected portion of the infrared illumination directly reflected from the region using a sensor positioned to receive the illumination directly reflected from the region, and generating at least one image indicative of the lymph nodes or lymphatic vessels in the subject using the reflected portion of the infrared illumination.

In a further aspect, a system for imaging a lymphatic component is provided. The system includes an optical source configured to provide infrared illumination having a polarization to a region of a subject having at least one lymphatic component, a sensor configured to sense a reflected portion of the infrared illumination having an opposite polarization to that of the polarization directly reflected from the region, generate at least one image indicative of the at least one lymphatic component in the subject based on the reflected portion of the infrared illumination, and output the at least one image to at least one of an external display or an external memory.

BRIEF DESCRIPTION OF THE DRAWINGS

FIG. 10A shows an exemplary image taken with an InGaAs camera when an illumination wavelength of 1000 nm was used.

FIG. 10B shows an exemplary image taken with an InGaAs camera when an illumination wavelength of 1175 nm was used.

FIG. 10C shows an exemplary image taken with an InGaAs camera when an illumination wavelength of 1250 nm was used.

FIG. 10D shows an exemplary image taken with an InGaAs camera when an illumination wavelength of 1375 nm was used.

FIG. 10E shows an exemplary image taken with an InGaAs camera when an illumination wavelength of 1550 nm was used.

DETAILED DESCRIPTION

Figure 1:
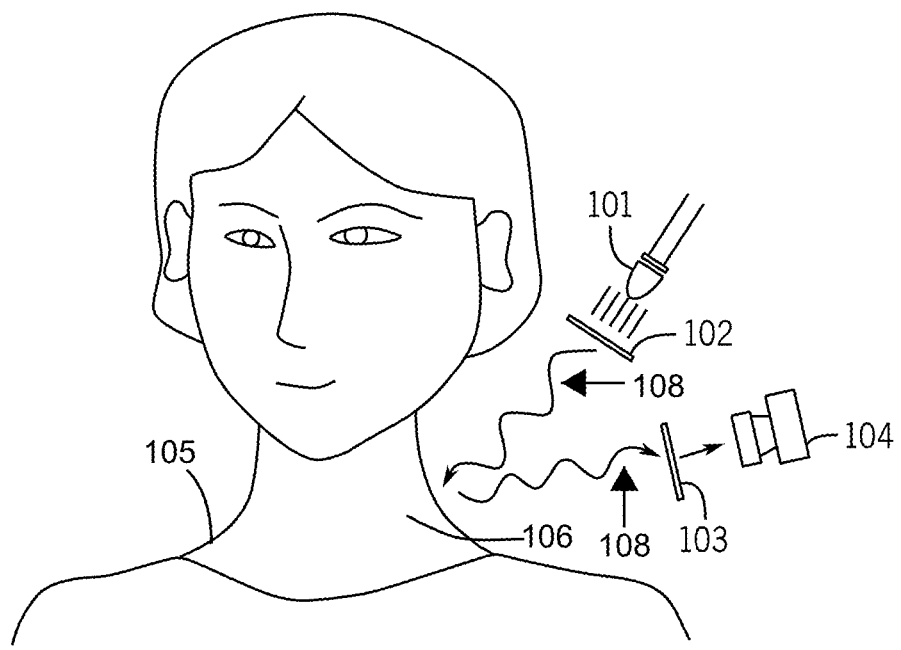
FIG. 1 shows a schematic diagram of an example of an imaging system in accordance with certain aspects of the present disclosure.

In one exemplary embodiment, depicted in FIG. 1, an imaging system 100 is provided for imaging lymphatic components. As used herein lymphatic components can include at least one of a lymph node or a lymphatic vessel. The imaging system 100 can include a LED light source 101 emitting between 900 and 1300 nm used as the light source. The LED light source 101 may also be referred to as the light source 101. The imaging system 100 can include a linear polarizer 102 mounted on a rotational mount and placed in front of the LED light source 101 to create linearly polarized illumination light 107 (i.e., illumination). The linear polarizer 102 can include linear polarizing film. The linearly polarized illumination 107 is shone onto a subject of interest 105, which can be either a human, as depicted in FIG. 1, or an animal.

The light source 101 can be oriented towards an in vivo target region 106 of the subject of interest 105. The in vivo target region 106 may also be referred to as an in vivo region or target region herein. In some embodiments, the target region 106 may be an ex vivo region such as a tissue portion. The ex vivo tissue portion may include fat, lymph nodes, and/or lymphatic vessels, and the lymph nodes, and/or lymphatic vessels can be imaged as if the tissue portion was in vivo.

Figure 7B:
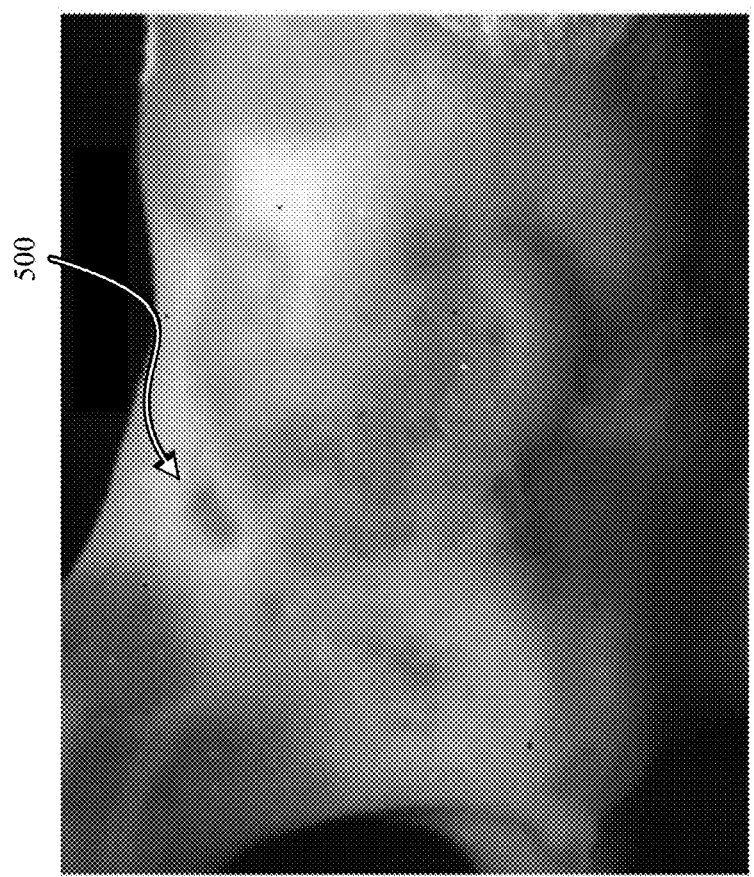
FIG. 7B shows imaging results of the same region as FIG. 7A imaged using polarizers.
Figure 7A:
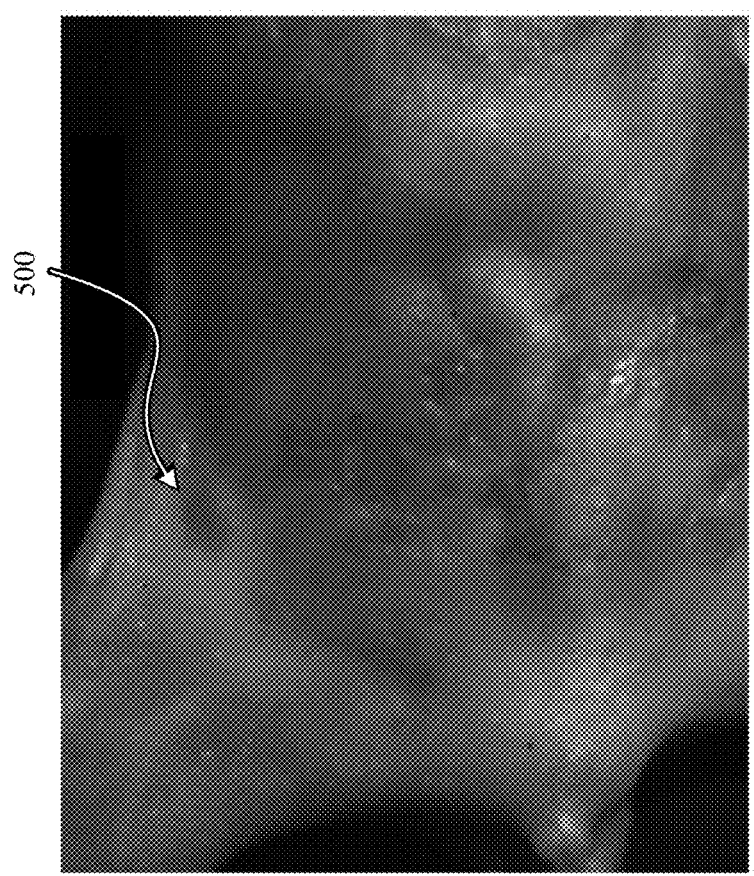
FIG. 7A shows imaging results of a region imaged without using polarizers.

Some light sources, such as certain lasers, are inherently linearly polarized. In the case of these inherently linearly polarized light sources, creating linearly polarized illumination does not require the use of linear polarizers. Thus, the linear polarizer 102 may not be required when the light source 101 is inherently linearly polarized. In other words, some imaging systems may not include the linear polarizer 102. Polarized illumination helps improve the imaging contrast of this technique, but is not necessary. A clear contrast of the lymph nodes can be formed even without any polarizers, as shown in FIGS. 7A-B.

Still referring to FIG. 1, the imaging system 100 can include a sensor 104, which can be a camera. The sensor 104 is used to visualize the illuminated area on a human or an animal. The light source can be oriented towards the target region 106 of the subject of interest 105. The imaging system 100 can include another linear polarizer 103, which may be referred to as the sensor linear polarizer 103. The sensor linear polarizer 104 can include linear polarizing film. The sensor linear polarizer 103 can be placed in front of the sensor 104 and/or positioned between the sensor 104 and the target region 106.

An ideal imaging contrast can be formed when the polarization of incoming light 108 before the sensor 104 and the polarizer 103 in front of the sensor 104 is orthogonal to the polarizer 103 in front of the sensor 104. The incoming light can include a portion of the linearly polarized illumination 107 that has interacted with tissues in the in vivo region 106. In principle, linearly polarized illumination remains mostly linearly polarized when reflecting off the surface of human or animal skin. The polarization of linearly polarized light does not change when bouncing directly away from the surface of the skin. Only a small portion of the light became randomly polarized, because it traveled relatively deeply into the biological tissues, which serves as randomly scattering media. By placing the sensor linear polarizer 103 in front of the sensor 104 orthogonal to the direction of the incoming light 108, the sensor linear polarizer 103 filters out the light reflected by the surface of human or animal skins and lets through only the portion of the light 107 emitted from light source 101 that interacted with deeper tissues. When the light reflected from the surface of the skin (i.e., surface glare) is reduced to the minimum level, the imaging system 100 achieves the best contrast and deepest penetration depth. In practice, this ideal contrast can be formed by rotating one of the polarizers, either the sensor linear polarizer 103 or the linear polanizer 102 in front of the light source 101, until the lowest overall intensity detected by the sensor 104 is reached. The lowest overall intensity can be associated with a threshold contrast level. The threshold contract level can be within a predetermined range of the lowest overall intensity, such as within ten percent of the lowest overall intensity, and the polarizer (e.g., the sensor linear polarizer 103 or the linear polarizer 102 in front of the light source 101) and/or light source 101 can be adjusted until the threshold contract level is achieved at the sensor 104.

After linearly polarized photons interact with tissue in the target region 106 and go through scattering, the linearly polarized photons slowly lose their linear polarization. After around, for example, ten scattering events, the linearly polarized photons become completely depolarized photons. These completely-depolarized photons then reach the sensor linear polarizer 103 in front of the sensor 104. Because the sensor linear polarizer 103 in front of the sensor 104 is approximately orthogonal to the linear polarizer 102 in front of the light source 101, only the photons that are now completely depolarized and have the opposite polarization are allowed to be detected by the sensor 104. Therefore, only the photons that interacted at a deeper level with the tissue in the target region 106 are "selected" to be analyzed, and surface glare and unnecessary surface features are removed.

When the wavelength of light emitted from the light source 101 is much longer than visible light (e.g., 1550 nm), imaging quality can be improved further. Longer wavelengths are associated with lower scattering effect. As a result, much thicker tissue is required to completely depolarize linearly polarized light with longer wavelengths as compared to linearly polarized light with shorter wavelengths. Imaging systems, such as the imaging system 100, can therefore provide light having longer wavelengths to the subject (e.g., the subject 105) in order better image deeper tissues as compared to shorter wavelengths (e.g., wavelengths in the visible light spectrum).

In the case that the light source 101 is a laser that is already linearly polarized without using a polarizer, the threshold contrast level be met by rotating either the sensor linear polarizer 103 or the laser itself. The relative orthogonal relationship is important and the absolute directions of polarization are not. The optimal contrast can be achieved through either rotating polarizers, light sources, or sensors, as long as the orthogonal polarization relationship is met. It is noted that the imaging system 100 of FIG. 1 does not require a mirror, and does not require a mirror or other reflective surface as is common in certain imaging techniques, which can reduce the cost to build the imaging system 100 of FIG. 1 as compared to other imaging techniques.

The present disclosure recognizes that lymph nodes are birefringent, i.e. responsive to polarized light. Lymph nodes and/or lymph vessels can contain collagen, which is birefringent. Furthermore, the tissues surrounding the lymph nodes such as layers of fat (i.e. lipids) are generally not birefringent. Thus, the present disclosure recognizes that cross-polarization, i.e. the orthogonal polarization relationship described above, can be used to exploit the difference in birefringence between lymph nodes and/or lymph vessels and the surrounding tissue in order to generate an image of the lymph nodes and/or lymph vessels. In some embodiments, the light source 101 may provide illumination with a wavelength of 1200-1600 nm, which can correspond to one or more absorption peaks of the collagen in lymph nodes and/or lymph vessels included in the target region 106. Using illumination wavelengths of 1200-1600 nm can therefore improve the imaging contrast between the lymph nodes and/or lymph vessels and the surrounding tissue. As described above, longer wavelengths may improve the imaging resolution of the lymph nodes and/or lymph vessels due to reduced scattering effects.

Additionally, illumination that includes longer wavelength light, especially 1550 nm wavelength light, can improve the contrast of lymphatic components in the target region 106. Generally, the lymphatic components are surrounded by fat. Lymph nodes and lymphatic vessels are high in water, while fat is very low in water. Absorption of photons occurs at 1550 nm in water, which is likely why using 1550 nm wavelength light to illuminate the target region 106 can improve the contrast (and therefore visibility) of the lymph nodes and/or lymphatic vessels in images generated using the imaging system 100. When generating images using 1550 nm illumination wavelength light, lymph nodes and lymphatic vessels appear dark, while fat is bright.

Furthermore, illumination that includes longer wavelength light, especially 1550 nm wavelength light, can improve the contrast of lymphatic components against surrounding blood in the target region 106. While blood contains a high amount of water, blood also contains a high amount of cells. The cells are highly scattering and overwhelm the water absorption effect. In testing, the imaging system 100 has been shown to generate images where blood and/or hemorrhage in the target region 106 are not visible, even compared to fat. Suppressing the visibility of blood and/or hemorrhage is an advantage of the imaging system 100 over other imaging modalities that generate images with visible blood and/or hemorrhages. Hemorrhages can be mistaken as lymph nodes, and are then harvested to be analyzed. Suppressing and/or removing hemorrhages from images may reduce the number of false positives that pathologists identify when diagnosing patients.

While the imaging system 100 has been described as being applied to an in vivo region of a subject, it is appreciated the imaging system can also be applied to an ex vivo tissue specimen as well. For example, the target region 106 can include a tissue packet that can include lymph nodes and fat. The tissue packet may have been removed from the subject 105 during a lymphadenectomy procedure performed after a tumor and relevant lymph nodes have been identified. The lymph nodes may then need to be separated from the fat and any other surrounding tissue included in the tissue packet during a grossing step. Typically, pathologists remove the lymph nodes via manual palpation and visual inspection, which is prone to error because lymph nodes are often translucent and appear similar to fat, lymph nodes may be as small as 1 mm across, and the locations of lymph nodes are often unpredictable. The imaging system 100 can be used to visualize the lymph nodes and display the lymph nodes to the pathologist, who can then efficiently and accurately remove the lymph nodes from the target region 106. Cancer organizations may require a certain number of lymph nodes to be examined for specific types of cancer. The number of lymph nodes required may range from twelve to thirty-eight. The imaging system 100 can, therefore, help the pathologist acquire the required number of lymph nodes by potentially reducing the number of lymph nodes missed in the target region 106.

Figure 2:
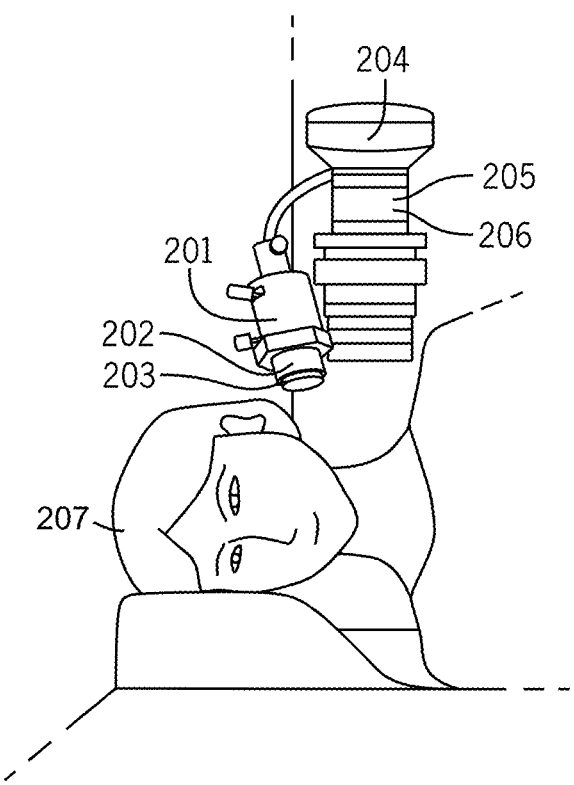
FIG. 2 illustrates another example of an imaging system in accordance with certain aspects of the present disclosure.

In FIG. 2, an illustration of another exemplary embodiment of an imaging system 200 is shown. In this exemplary imaging system 200, a halogen lamp with continuous light illumination is used as a light source 201. In order to reduce background from direct reflection at wavelengths out of the range of 900-1300 nm, longpass filters with cut-off wavelengths at 900 nm or 1000 nm are used to filter out light with shorter wavelengths. The imaging system 200 can include a primary longpass filter 203 and a secondary longpass filter 205. Each of the primary longpass filter 203 and the secondary longpass filter 205 can have a cut-off wavelength selected from 900 nm to 1000 nm, inclusive. The imaging system 200 can include a linear polarizer 202 on a screw mount. The linear polarizer 202 can include linear polarizing film. The linear polarizer 202 can be placed in front of the light source 201 to make the illumination light from the light source 201 (e.g., the halogen lamp) linearly polarized. The primary longpass filter 203 can be placed in front of light source 201 in order to filter out as much light emitted from the light source 201 that is below the cut-off wavelength as possible.

A regular commercially available silicon camera is used as a sensor 204 included in the imaging system 200. In some embodiments, a black silicon camera and/or an InGaAs camera can be used as the sensor 204. A sensor linear polarizer 206 is placed in front of the sensor 204 on a screw mount. The sensor linear polarizer 206 can include linear polarizing film. A lens (not shown), which may be a telecentric lens, is also placed in front of the sensor 204 to form an image. The telecentric lens can enhance the measurement accuracy of the imaging system 200 by helping to normalize the size of a lymph node in an image generated using the sensor 204 regardless of how far away the lymph node is from the sensor 204. The primary longpass filter 203 was also placed in front of the sensor 204 to filter out the unwanted background from either ambient light or the light source 201 (e.g., the halogen lamp). In some embodiments, there may not be a need to calibrate the sensor 204 for different ambient and/or background light amounts because the secondary longpass filter 205 can eliminate background light, which may include visible frequencies below the cutoff frequency of the secondary longpass filter 205. Eliminating the need to calibrate the sensor 204 can save time in detecting the lymphatic components, as well as make the imaging system 200 more robust as compared to an imaging system that requires calibration of one or more sensors. The light source 201 and the sensor 204 should both point at the same area of interest on the subject being studied, either a human or an animal, such as a person 207 as shown in FIG. 2. It is noted that the imaging system 200 of FIG. 2 does not include a mirror, and does not require a mirror or other reflective surface as is common in certain imaging techniques. This can reduce the cost to build the imaging system 200 of FIG. 2 as compared to other imaging systems and/or techniques.

In some embodiments, a controller (not shown) may be included in the imaging system 200. The controller can be coupled to an optical source such as a laser or LED, as well as a sensor such as a camera. The controller can be coupled to and in communication with the optical source and the sensor. The controller can be configured to cause the optical source to provide the infrared illumination to the region by controlling power supplied to the optical source. The controller can also receive information from the sensor corresponding to the infrared illumination reflected from the subject. The infrared illumination reflected can be referred to as a reflected portion of the infrared illumination that was originally supplied by the optical source. The controller can also generate at least one image indicative of the lymph nodes in the subject using the information received.

Figure 3:
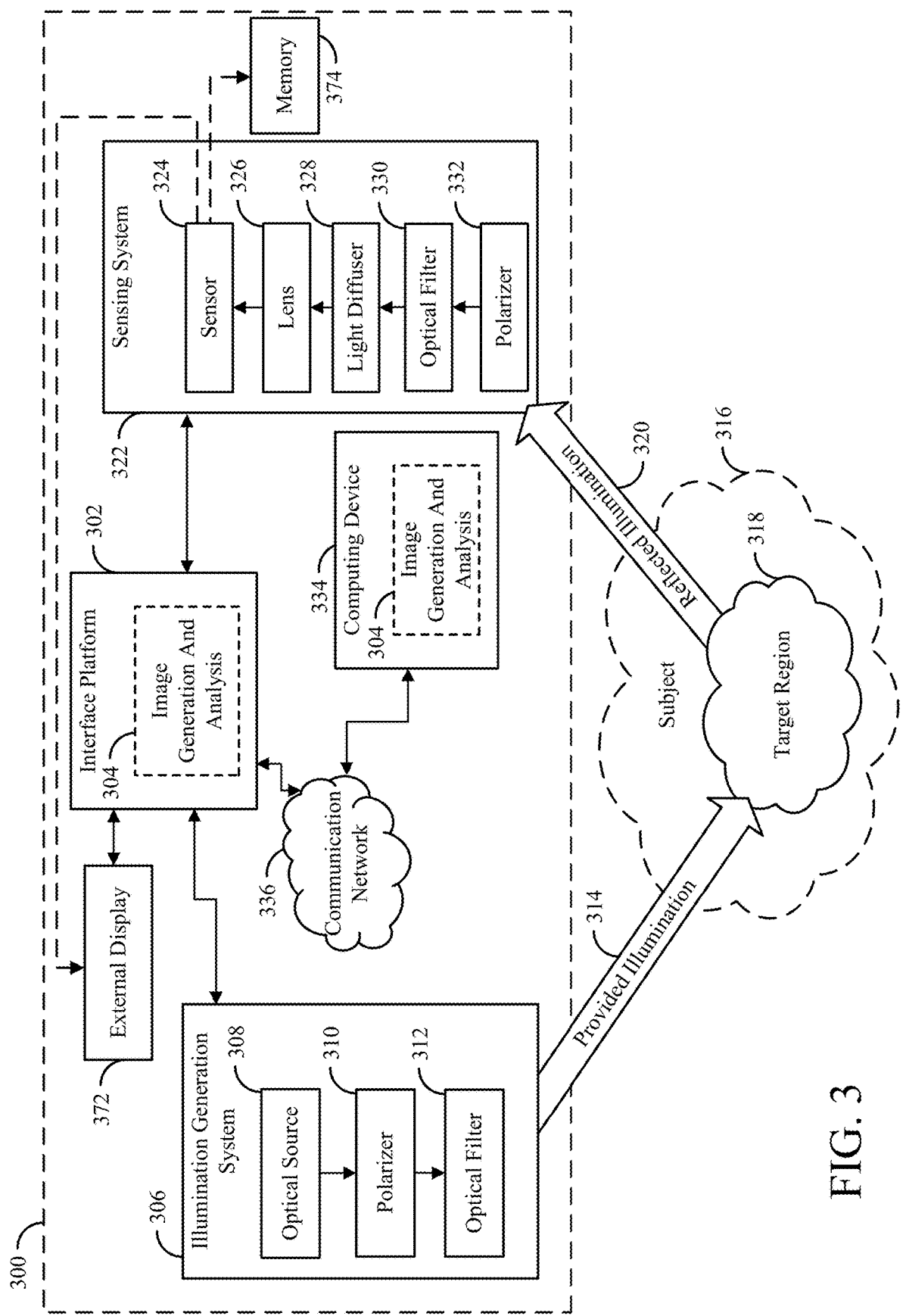
FIG. 3 shows a schematic diagram of yet another exemplary embodiment of an imaging system in accordance with certain aspects of the present disclosure.

Referring now to FIGS. 1 and 2 as well as FIG. 3, a schematic diagram of yet another exemplary embodiment of an imaging system 300 is shown. In some embodiments, the imaging system 300 can be approximately the size of a shoebox, and can therefore be a bench-top imaging device. The imaging system 300 can include an interface platform 302. The interface platform 302 can include at least one memory, at least one processor, and any number of connection interfaces capable of communication with sensors and optical sources (not shown). The interface platform 302 can also store (e.g., in the at least one memory) and execute (e.g., using the at least one processor) at least a portion of an image generation and analysis application 304. As will be described below, the interface platform 302 can be coupled to and in communication with a computing device 334 included in the imaging system 300 that may also store and/or execute at least a portion of the image generation and analysis application 304. The interface platform 302 can be a controller, a laptop computer, a desktop computer, or another device capable of receiving signals from a sensor and outputting control signals to an optical source. The controller can be a microcontroller, such as a Raspberry Pi 4 Model B. In some embodiments, the controller can be an Intel® NUC computer configured to operate using a Windows operating system.

The interface platform 302 can be coupled to and in communication with an illumination generation system 306 included in the imaging system 300. The illumination generation system 306 can include an optical source 308. The interface platform 302 can be coupled to and in communication with the optical source 308. The interface platform 302 can output control signals to the optical source 308 in order to cause the optical source 308 to provide illumination. In some embodiments, the optical source 308 may output suitable data (e.g., total lifetime hours of operation) to the interface platform 302. The illumination generation system 306, and more specifically, the optical source 308, can be oriented to provide illumination 314 to a target region 318 that may be in vivo (e.g., included in a subject 316 such as a patient) or ex vivo, as will be described further below. The illumination 314 output by the illumination generation system 306 can be referred to as the provided illumination 314. The illumination 314 can be infrared illumination. The infrared illumination can include light in the near-infrared range (800-1400 nm wavelength) and/or light in the short-wave infrared range (1400-3000 nm wavelength).

The optical source 308 can include at least one of an LED such as a single LED, a plurality of LEDs such as an LED array, a halogen lamp such as a tungsten halogen lamp, a quartz-halogen lamp, or a quartz iodine lamp, a laser, or another suitable optical source capable of outputting light at one or more predetermined wavelengths. In some embodiments, the optical source 308 may output one or more discrete wavelengths of light, such as 1550 nm, 1375 nm, 1300 nm, and/or other wavelengths selected from 800 nm to 1700 nm wavelengths. For example, the optical source 308 may only output 1550 nm wavelength light. In some embodiments, the optical source can output one or more discrete frequencies from a subrange of wavelengths within the 800 nm to 2000 nm range, such as a subrange of 1200-1600 nm wavelengths. In some embodiments, the optical source 308 may output a continuous range of wavelengths of light, such as 900-1300 nm, 1500-1600 nm, 1200-1600 nm, 1000-1700 nm (i.e., near-infrared), and/or other ranges of wavelengths within 800-2000 nm. In some embodiments, the optical source 308 may be the light source 101 of FIG. 1 or the light source 201 of FIG. 2. In particular, the optical source 308 may output longer wavelength light, especially 1550 nm wavelength light, in order to better contrast lymphatic components against surrounding fat, blood, and/or hemorrhages as described above. For the imaging system 300 to function properly, the optical source 308 does not need to emit a range of wavelengths of light. In testing, excellent imaging has been obtained using only 1550 nm wavelength light. However, the imaging system 300 can perform suitable imaging using multiple wavelengths of light. It is contemplated that light with wavelengths up to 2600 nm could be used, as some sensors such as certain InGaAs cameras stop responding beyond 2600 nm. Thus, light with wavelengths ranging from 800-2600 nm might be used in the imaging system 300. In testing, light with wavelengths below 800 nm has not performed as well as light with higher wavelengths, such as 800-1700 nm.

In some embodiments, the illumination generation system 306 can include a polarizer 310 such as a linear polarizer. For certain optical sources that are not inherently polarized, such as halogen optical sources, the imaging system 300 may include a polarizer 310. The polarizer 310 can include linear polarizing film. The polarizer 310 can be mounted and placed in front of the optical source 310 to create linearly polarized illumination light. The polarizer 310 can be mounted on a rotational mount or other suitable mount to allow for adjustment of the polarizer 310. Thus, the illumination 314 provided to the target region 318 can be linearly polarized. Polarized illumination can improve imaging contrast in images generated by the imaging system 300, but it is not necessary. In some embodiments, the polarizer 310 may be the linear polarizer 102 of FIG. 1 or the linear polarizer 202 of FIG. 2. If the optical source 308 is an inherently polarized device, such as certain lasers, the polarizer 310 may not be included in the imaging system 300. In some embodiments, the polarizer 310 can be a circular polarizer.

In some embodiments, the illumination generation system 306 can include an optical filter 312. The optical filter 312 can be a longpass filter such as a cold mirror, a colored glass filter, a thermoset allyl diglycol carbonate (ADC) filter, or another suitable filter capable of attenuating lower wavelength light (e.g., visible light) and passing higher wavelength light (e.g., infrared light). The longpass filter may have a cut-off wavelength of no less than 800 nm. For example, the cut-off wavelength may be 800 nm, 900 nm, or 1000 nm. The optical filter 312 can be placed in front of light source optical source 308 in order to filter out as much light emitted from the optical source 308 that is below the cut-off wavelength as possible. In some embodiments, the optical filter 312 may be the primary longpass filter 203 of FIG. 2. In some embodiments, the optical filter 312 can be a bandpass filter such as a hard coated filter or a colored glass filter. The bandpass filter may only pass a range of light wavelengths within a 800-2000 nm window, or a subrange of the 800-2000 nm window. For example, the bandpass filter may only pass 900-1700 nm wavelength light. Thus, the illumination 314 provided to the target region 318 can be longpass filtered or bandpass filtered.

The optical source 308, the polarizer 310, and/or the optical filter 312 can be physically arranged (i.e., positioned) relative to each other as shown in FIG. 1 and/or FIG. 2. For example, the optical source 308 and the polarizer 310 can be arranged in similar fashion to the light source 101 and the linear polarizer 102, respectively, as shown in FIG. 1. As another example, the optical source 308, the polarizer 310, and the optical filter 312 can be arranged in similar fashion to the light source 201, the linear polarizer 202, and the longpass filter 203, respectively, as shown in FIG. 2. The optical source 308 can output the illumination 314 that may pass through and be polarized by the polarizer 310 and/or pass through and be attenuated by the optical filter 312. The illumination 314 which may be polarized and/or attenuated, is then provided to the target region 318.

As mentioned above, the optical source 308, and by extension the illumination generation system 306, can be oriented to provide the illumination 314 to the target region 318. In some embodiments, the target region 318 can be an in vivo region included in the subject 316. In these embodiments, the target region 318 may be referred to as the in vivo region. The subject 316 can be a human patient. In other embodiments, the target region 318 can be an ex vivo region. In these embodiments, the target region 318 may be referred to as the ex vivo region. For example, the target region 318 can be a tissue portion removed from a subject for grossing purposes as described above. The imaging system 300 can be used to aid in the grossing of the tissue portion by visualizing lymphatic components for a practitioner.

At least a portion of the illumination 314 can be provided to the target region 318. The target region 318 may include one or more lymphatic components. The provided illumination 314 can interact with the lymphatic components and the surrounding tissue in the target region 318. At least a portion of the provided illumination 314 may become randomly polarized as described above. At least a portion of the provided illumination 314 can be reflected as reflected illumination 320. The reflected illumination 320 can include light that has interacted with deep tissue in the target region 318.

The interface platform 302 can be coupled to and in communication with a sensing system 322 included in the imaging system 300. The sensing system 322 can include a sensor 324. The interface platform 302 can be coupled to and in communication with the sensor 324. The sensor 324 can sense the reflected illumination 320 and output signals associated with an image based on the sensed reflected illumination 320. The interface platform 302 can receive the signals indicative of the image from the sensor 324. The signals can include information about the image. In some embodiments, the information can include the image formatted in a predetermined image format such as PNG, JPEG, DICOM (i.e., included in a DICOM file), etc. In some embodiments, the information can also include metadata about the image, such as the time the image was taken or a patient associated with the image. In some embodiments, the sensor 324 can include a camera, such as a silicon camera including a silicon complementary metal oxide semiconductor (CMOS) camera or a silicon charge-coupled device (CCD) camera with phosphor coating, a germanium camera, a germanium-tin on silicon camera, a black silicon camera, a quantum dot shortwave infrared (SWIR) camera, and/or an InGaAs camera. The InGaAs camera may be a nitrogen cooled InGaAs camera. The sensor 324 can include a mercury-cadmium-telluride (HgCdTe or MCT) camera. The sensor 324 can be responsive to light including at least a portion of the light ranging from 800 nm-2000 nm in wavelength, especially wavelengths at or near 1550 nm. It is noted that the imaging system 300 may only require a single sensor (e.g., a silicon camera), in contrast to other systems that may require multiple sensors and/or cameras.

The sensing system 322 can include a lens 326 positioned in front of the sensor 324. In some embodiments, the lens 326 can be integral with the sensor 324, such as if the sensor 324 and the lens 326 are sold as a single off-the-shelf component. The lens 326 can improve the imaging capabilities of the sensor 324. For example, the lens 326 can be a telecentric lens. The telecentric lens can enhance the measurement accuracy of the imaging system 300 by helping to normalize the size of a lymph node in an image generated using the sensor 324 regardless of how far away the lymph node is from the sensor 324.

In some embodiments, the sensing system 300 can include a light diffuser 328 such as a piece of frosted glass or a tissue paper. The light diffuser 328 can be inserted between the lens 326 and a polarizer 332 that can be included in the sensing system 322. The light diffuser 328 can create a more evenly distributed light pattern in the reflected illumination 320. The light diffuser 328 may improve the imaging capabilities of the sensor 324 as a result of the more evenly distributed light pattern.

In some embodiments, the sensing system 322 can include an optical filter 330 positioned in front of the sensor 324. The optical filter 330 can be a longpass filter such as a cold mirror, a colored glass filter, a thermoset ADC filter, or another suitable filter capable of attenuating lower wavelength light (e.g., visible light) and passing higher wavelength light (e.g., infrared light). The longpass filter can have a cut-off wavelength of no less than 800 nm. For example, the cut-off wavelength may be 800 nm, 900 nm, or 1000 nm. In some embodiments, there may not be a need to calibrate the sensor 324 for different ambient and/or background light amounts because the optical filter 330 can eliminate background light, which may include visible frequencies below the cutoff frequency of the optical filter 330. In some embodiments, the optical filter 330 may be the secondary longpass filter 205 as shown in FIG. 2. In some embodiments, the optical filter 330 can be a bandpass filter such as a hard coated filter or a colored glass filter. The bandpass filter may only pass a range of light wavelengths within a 800-2000 nm window, or a subrange of the 800-2000 nm window. For example, the bandpass filter may only pass 900-1700 nm wavelength light. Thus, the reflected illumination 320 provided to the sensor 324 can be longpass filtered or bandpass filtered.

As mentioned above, the sensing system can include the polarizer 332. The polarizer 332 can be a linear polarizer. In some embodiments, the polarizer 332 can be a circular polarizer. The polarizer 332 can be placed in front of the sensor 324. The polarizer 332 can include linear polarizing film. Similar to the polarizer 310 included in the illumination generation system 306, the polarizer 332 included in the sensing system 322 can be mounted on a rotational mount or other suitable mount to allow for adjustment. The linear polarizers 310, 332, can be rotated or otherwise adjusted to create an ideal imaging contrast as described above. The polarizer 332 can remove any light having the same polarization as the provided illumination 314 from the reflected illumination 320. The sensor 324 can detect light included in the reflected illumination 320 having the opposite polarization as the provided illumination 314.

In some embodiments, the sensor 324 can be coupled to and in communication with the external display 372. Alternatively or in addition, the sensor 324 can be coupled to and in communication with a memory 374 that may be included in the imaging system 300 or external to the imaging system 300. For example, the memory 374 can be flash memory included in a memory card. In embodiments where the sensor 324 is coupled to and in communication with the external display 372 and/or the memory 374, the sensor 324 can be configured to sense the reflected portion of the provided illumination 314 and generate at least one image indicative of the any lymphatic components in the target region 318 based on the reflected portion (i.e., the reflected illumination 320) of the provided illumination 314. The sensor 324 may also be configured to output the at least one image to at least one of the external display 372 or the memory 374.

In some embodiments, the optical source 308 may not be coupled to a controller or other device, and may only need to be coupled to a power source. In these embodiments, the optical source 308 can provide the illumination 314 to the target region 318 constantly or semi-constantly. In some embodiments, the interface platform 304 can supply power to the optical source 308 (i.e., act as the power source). In other embodiments, the optical source 308 can receive power from wall power, one or more batteries, or another suitable power source.

In some embodiments, the sensor 324 can be coupled to the external display 372 and/or the memory 374, and the optical source may be coupled to a power supply without being coupled to the interface platform 304 and/or other suitable device. Thus, the imaging system 300 can be implemented without the use of a controller or computational device.

In some embodiments, the imaging system 300 can be Class-1, 510(k)-exempt, and/or good manufacturing practice (GMP) exempt.

The imaging system 300 may also include the external display 372 and/or the computing device 334. As mentioned above, the interface platform 302 can be coupled to and in communication with the computing device 334. The imaging system 300 can include a communication network 336. The communication network 336 can facilitate communication between the interface platform 302 and the computing device 334. The interface platform 302 can also be coupled to and in communication with the external display 372.

In some embodiments, communication network 336 can be any suitable communication network or combination of communication networks. For example, communication network 336 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 336 can be a local area network, a wide area network, a public network (e.g., the Internet), a private or semi-private network (e.g., a corporate or university intranet), any other suitable type of network, or any suitable combination of networks. Communications links shown in FIG. 3 can each be any suitable communications link or combination of communications links, such as wired links, fiber optic links, Wi-Fi links, Bluetooth links, cellular links, etc. In some embodiments, the computing device 334 can implement portions of the image generation and analysis application 304.

Figure 4:
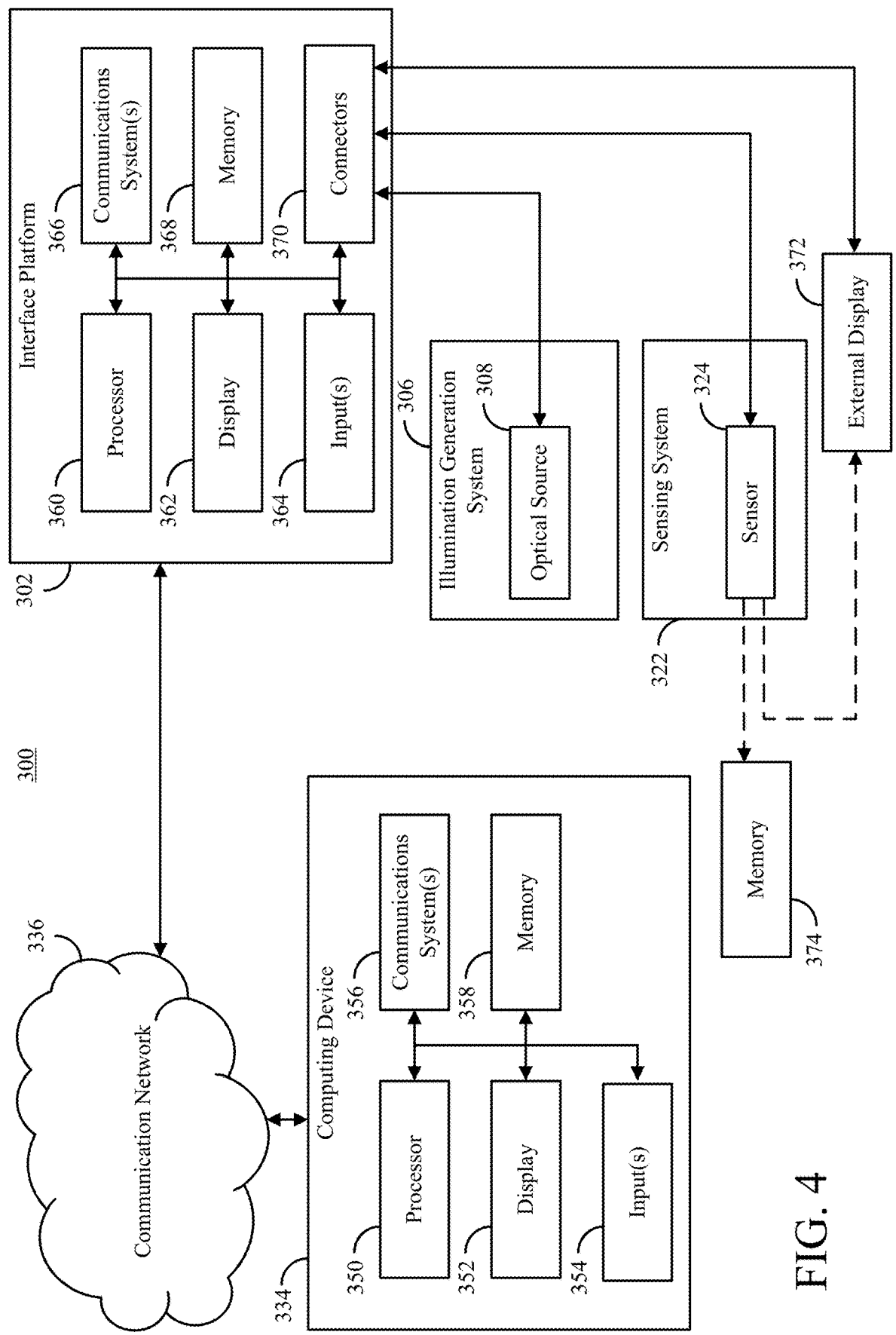
FIG. 4 shows an example of hardware that can be used to implement a computing device and an interface platform shown in FIG. 3 in accordance with some embodiments of the disclosed subject matter.

Referring now to FIG. 3 as well as FIG. 4, an example of hardware that can be used to implement a computing device 334 and an interface platform 302 shown in FIG. 3 in accordance with some embodiments of the disclosed subject matter is shown. As shown in FIG. 4, the computing device 334 can include a processor 350, a display 352, an input 354, a communication system 356, and memory 358. The processor 350 can implement at least a portion of the image generation and analysis application 304, which can, for example be executed from a program (e.g., saved and retrieved from memory 358). The processor 350 can be any suitable hardware processor or combination of processors, such as a central processing unit ("CPU"), a graphics processing unit ("GPU"), etc., which can execute a program, which can include the processes described below.

In some embodiments, the display 352 can present a graphical user interface. In some embodiments, the display 352 can be implemented using any suitable display devices, such as a computer monitor, a touchscreen, a television, etc. In some embodiments, the inputs 354 of the computing device 334 can include indicators, sensors, actuatable buttons, a keyboard, a mouse, a graphical user interface, a touch-screen display, etc. In some embodiments, the inputs 354 can allow a user (e.g., a medical practitioner, such as a radiologist) to interact with the computing device 334, and thereby to interact with the interface platform 302 (e.g., via the communication network 336).

In some embodiments, the communication system 356 can include any suitable hardware, firmware, and/or software for communicating with the other systems, over any suitable communication networks. For example, the communication system 356 can include one or more transceivers, one or more communication chips and/or chip sets, etc. In a more particular example, communication system 356 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 356 allows the computing device 334 to communicate with the interface platform 302 (e.g., directly, or indirectly such as via the communication network 336).

In some embodiments, the memory 358 can include any suitable storage device or devices that can be used to store instructions, values, etc., that can be used, for example, by processor 350 to present content using display 352, to communicate with the interface platform 302 via communications system(s) 356, etc. Memory 358 can include any suitable volatile memory, non-volatile memory, storage, or any suitable combination thereof. For example, memory 358 can include RAM, ROM, EEPROM, one or more flash drives, one or more hard disks, one or more solid state drives, one or more optical drives, etc. In some embodiments, memory 358 can have encoded thereon a computer program for controlling operation of computing device 334 (or interface platform 302). In such embodiments, processor 350 can execute at least a portion of the computer program to present content (e.g., user interfaces, images, graphics, tables, reports, etc.), receive content from the interface platform 302, transmit information to the interface platform 302, etc.

As shown in FIG. 4, the interface platform 302 can include a processor 360, a display 362, an input 364, a communication system 366, memory 368, and connectors 370. In some embodiments, the processor 360 can implement at least a portion of the image generation and analysis application 304, which can, for example be executed from a program (e.g., saved and retrieved from memory 368). The processor 360 can be any suitable hardware processor or combination of processors, such as a central processing unit ("CPU"), a graphics processing unit ("GPU"), etc., which can execute a program, which can include the processes described below.

In some embodiments, the display 362 can present a graphical user interface. In some embodiments, the display 362 can include any suitable display devices, such as a computer monitor, a touchscreen, a television, etc. In some embodiments, the inputs 364 of the interface platform 302 can include indicators, sensors, actuatable buttons, a keyboard, a mouse, a graphical user interface, a touch-screen display, and the like. In some embodiments, the inputs 364 allow a user (e.g., a first responder) to interact with the interface platform 302, and thereby to interact with the computing device 334 (e.g., via the communication network 336). The computing device 334 can also be coupled to and in communication with an external display 372 that can provide at least some of the functionality of the display 352.

As shown in FIG. 4, the interface platform 302 can include the communication system 366. The communication system 366 can include any suitable hardware, firmware, and/or software for communicating with the other systems, over any suitable communication networks. For example, the communication system 366 can include one or more transceivers, one or more communication chips and/or chip sets, etc. In a more particular example, communication system 366 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 366 allows the interface platform 302 to communicate with the computing device 334 (e.g., directly, or indirectly such as via the communication network 336). It is contemplated that the communication system 366 could communicate with the optical source and/or the sensor 324, and thus provide at least some of the functionality of the connectors 370, which will be described below.

In some embodiments, the memory 368 can include any suitable storage device or devices that can be used to store instructions, values, etc., that can be used, for example, by processor 360 to present content using display 362, to communicate with the computing device 334 via communications system(s) 366, etc. Memory 368 can include any suitable volatile memory, non-volatile memory, storage, or any suitable combination thereof. For example, memory 368 can include RAM, ROM, EEPROM, one or more flash drives, one or more hard disks, one or more solid state drives, one or more optical drives, etc. In some embodiments, memory 368 can have encoded thereon a computer program for controlling operation of the interface platform 302 (or computing device 334). In such embodiments, processor 360 can execute at least a portion of the computer program to present content (e.g., user interfaces, graphics, tables, reports, etc.), receive content from the computing device 334, transmit information to the computing device 334, etc.

In some embodiments, the connectors 370 can be wired connections, such that the optical source 308 and the sensor 324 can communicate with the interface platform 302, and thus can communicate with the computing device 334 (e.g., via the communication system 366 and being directly, or indirectly, such as via the communication network 336). Additionally or alternatively, the optical source 308 and/or the sensor 324 can send information to and/or receive information from the interface platform 302 (e.g., using the connectors 370, and/or the communication systems 366).

Figure 5:
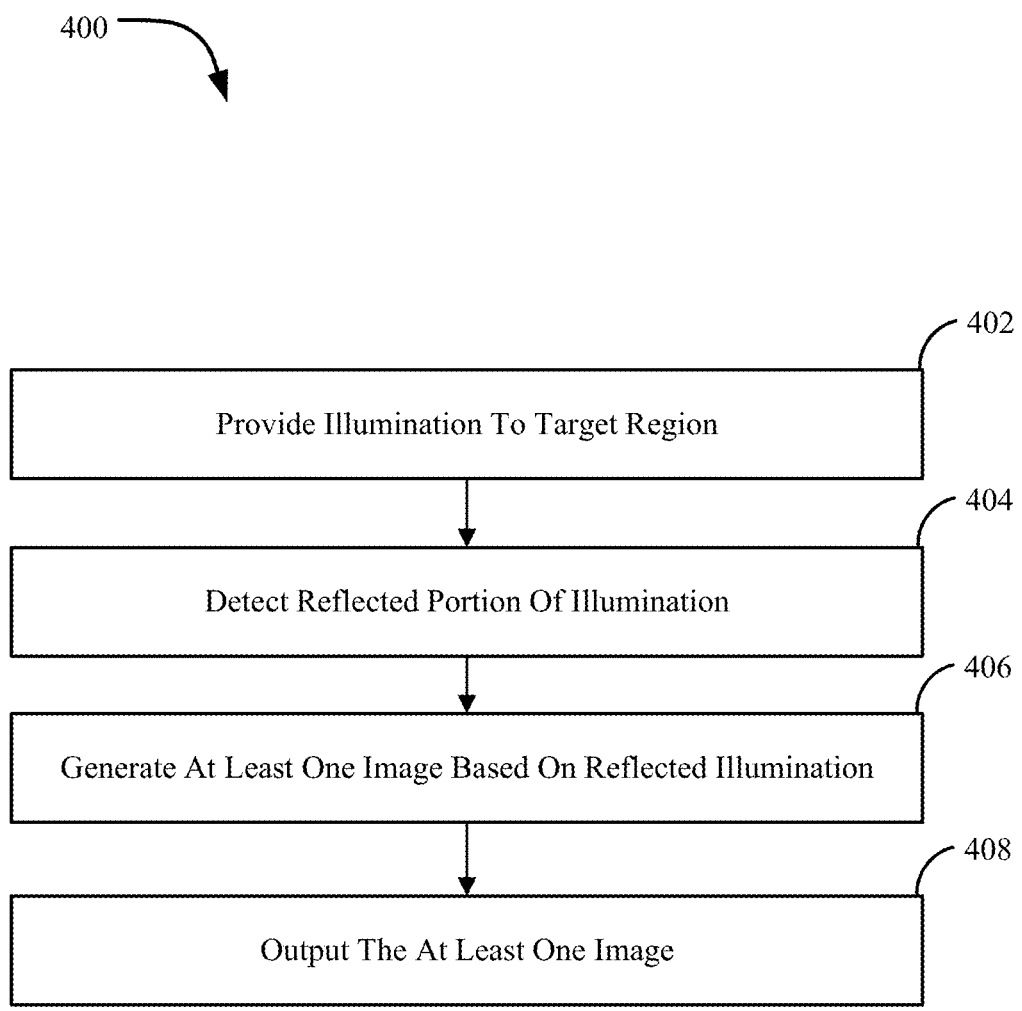
FIG. 5 shows an exemplary flowchart of a process included in an image generation and analysis application.

Referring now to FIGS. 3-4 as well as FIG. 5, an exemplary flowchart of a process 400 included in the image generation and analysis application 304 is shown. In some embodiments, the interface platform 302 and the computing device 334 may each execute a portion of the process 400 in order to generate images of the target region 318, which may contain lymphatic components, such as lymph nodes and/or lymphatic vessels. As described above, the target region 318 can be in vivo (e.g., included in the subject 316) or ex vivo (e.g., a tissue packet removed from a subject). In some embodiments, the interface platform 302 may execute the entire process 400.

At 402, the process 400 can cause the optical source 308 to provide the illumination 314 to the target region 318. The target region 318 may include lymphatic components. The provided illumination 314 may pass through the polarizer 310 and/or the optical filter 312. The provided illumination 314 is then provided to the target region 318. At least a portion of the provided illumination 314 can then be reflected as the reflected illumination 320 towards the sensing system 322, as described above. The reflected illumination 320 may pass through the polarizer 332, the optical filter 330, the light diffuser 328, and/or the lens 326 before reaching the sensor 324. In some embodiments, the process 400 may not need to cause the optical source 308 to provide illumination if the optical source 308 is continuously or semi-continuously providing the illumination 314 to the target region 318. In other words, in some embodiments, the process 400 may not implement step 402.

At 404, the process 400 can detect a reflected portion of the illumination 314. The reflected portion can be the reflected illumination 320. The reflected portion can be directly reflected from the target region 318. Because the reflected portion is directly reflected from the target region 318, the system 300 does not require the use of a mirror or other reflector to redirect the reflected portion towards the sensor 324. The process 404 can detect the reflected portion using the sensor 324. Detecting the reflected portion of the illumination 314 can include receiving signals from the sensor 324 in response to the reflected portion.

At 406, the process 400 can generate at least one image indicative of one or more lymphatic components, such as lymph nodes and lymphatic vessels, if present in the target region 318 using the reflected portion of the illumination 314. The process 400 may generate the at least one image based on the signals received from the sensor 324 at 404. The process 400 may generate the image based on the signals from the sensor 324. In some embodiments, the signals output by the sensor 324 can include the at least one image indicative of the lymphatic components. The process 400 may reformat and/or compress the at least one image received from the sensor. Alternatively, the process 400 may store the at least one image (i.e., in the memory 358 and/or the memory 368) as received from the sensor 324.

At 408, the process 400 can output the at least one image to at least one of a display and/or a memory. The display can be the display 362 that can be included in the interface platform 302, the display 352 that can be included in the computational device 334, or the external display 372. The memory can be the memory 368 included in the interface platform 302 or the memory 358 included in the computing device 334. The memory can be a memory outside the imaging system 300, such as a memory included in a remote server.

Figure 6:
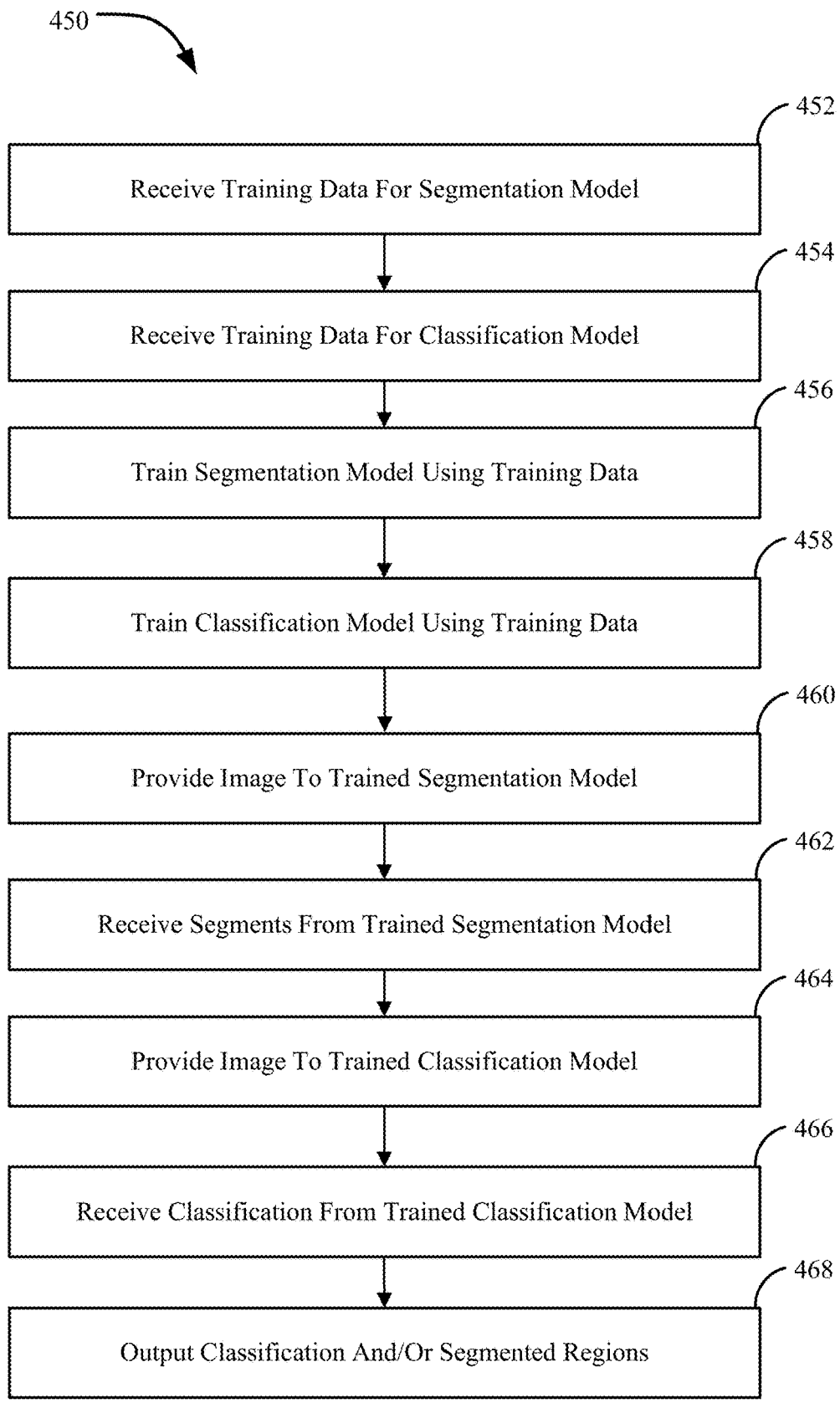
FIG. 6 shows an exemplary flowchart of another process included in the image generation and analysis application.

Referring now to FIGS. 3-4 as well as FIG. 6, an exemplary flowchart of a process 450 included in the image generation and analysis application 304 is shown. In some embodiments, the interface platform 302 and the computing device 334 may each execute a portion of the process 450 in to train a segmentation machine learning model and/or a classification machine learning model, as well as analyze images produced by an imaging system (e.g., the imaging system 300 in FIG. 3 and FIG. 4) using the segmentation machine learning model and/or the classification machine learning model after the model(s) have been trained.

At 452, the process 450 can receive training data for a segmentation model. The segmentation model can be a machine learning model such as a convolutional neural network. The convolutional neural network may include U-Net network architecture. The training data for the segmentation model can include raw images and associated segments. The raw images can be generated using an imaging system such as the imaging system 100 in FIG. 1, the imaging system 200 in FIG. 1, or the imaging system 300 in FIG. 3. The segments can be areas of the images that either correspond to lymph nodes or the absence of lymph nodes. In some embodiments, the segments can also include areas that correspond to lymphatic vessels. Thus, the segmentation model can be trained to segment lymph nodes and lymphatic vessels in images. The segments can be previously identified by a qualified practitioner such as an oncologist. In some embodiments, the segmentation model can be a predetermined algorithm configured to identify lymph nodes that may not require training.

At 454, the process 450 can receive training data for a classification model. The classification model can be a machine learning model such as a recurrent neural network. The classification model can be trained to classify entire images. The training data for the classification model can include a number of raw images generated using an imaging system such as the imaging system 100 in FIG. 1, the imaging system 200 in FIG. 1, or the imaging system 300 in FIG. 3. The training data can also include a number of segmented images corresponding to the number of raw images. The segmented images can be produced by providing the raw images to the trained segmentation model. In some embodiments, the training data can include a classification of each segmented lymph node and/or lymphatic vessels. The classification can be malignant or healthy, and can be provided by a suitable medical practitioner. In some embodiments, each classification can be associated with an entire raw image included in the training data.

At 456, the process 450 can train the segmentation model using the training data for the segmentation model. After the segmentation model is trained at 456, the segmentation model can be referred to as the trained segmentation model.

At 458, the process 450 can train the classification model using the training data for the classification model. Depending on the training data, the classification model can be trained to identify individual lymphatic components (i.e., lymph nodes and/or lymphatic vessels) as malignant or healthy, or trained to identify entire images as healthy or malignant. After the classification model is trained at 456, the classification model can be referred to as the trained classification model.

At 460, the process 450 can provide an image to the trained segmentation model. In some embodiments, the process 450 can sequentially provide any number of images to the trained segmentation model at 460.

At 462, the process 450 can receive a number of segments associated with the image provided to the trained segmentation model. In some embodiments, the process 450 can receive a number of segments for each image provided to the trained segmentation model at 460.

At 464, the process 450 can provide an image to the trained classification model. In some embodiments, the process 450 can sequentially provide any number of images to the trained classification model at 464.

At 466, the process 450 can receive a classification for the image provided to the trained classification model. In some embodiments, the process 450 can receive a number of classification associated with the number of images provided to the trained model at 464.

At 468, the process 450 can output any received segment(s) and/or classification(s) to at least one of a display and/or memory. The display can be the display 362 that can be included in the interface platform 302, the display 352 that can be included in the computational device 334, or the external display 372. The memory can be the memory 368 included in the interface platform 302 or the memory 358 included in the computing device 334. The memory can be a memory outside the imaging system 300, such as a memory included in a remote server. External processes may perform further analysis on the received segments. For example, the segments can be used to determine features of each segmented lymphatic component, including lymph node size, lymph node aspect ratio, lymph node symmetry, lymph node border clarity, lymph node curvature, and/or lymphatic vessel patterns. Further analysis can be performed on the features of each lymphatic component. In some embodiments, the process 450 can output a heat map for each image identifying distinguishing features in each raw image (and, by extension, the lymphatic components) that led to the classifications for each lymphatic component and/or raw image.

It is understood that the image generation and analysis application 304 may include one or both of the process 400 of FIG. 5 and the process 450 of FIG. 6. In some embodiments, multiple applications may be implemented in order to execute one or both of the process 400 of FIG. 5 and the process 450 of FIG. 6.

FIGS. 7A and 7B show imaging results of an imaging system constructed in accordance with the imaging systems described herein. FIG. 7A shows imaging results of a region imaged without using polarizers. FIG. 7B shows imaging results of the same region imaged using polarizers. The region shown in FIGS. 7A and 7B includes a lymph node 500. The polarizers improve imaging contrast, but lymph nodes can be visualized with or without polarizers.

Figure 8A:
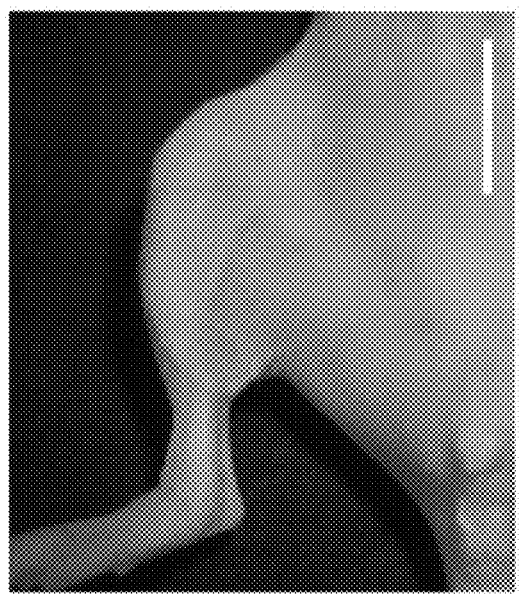
FIG. 8A shows an image of a region of a mouse taken with a standard camera.
Figure 8B:
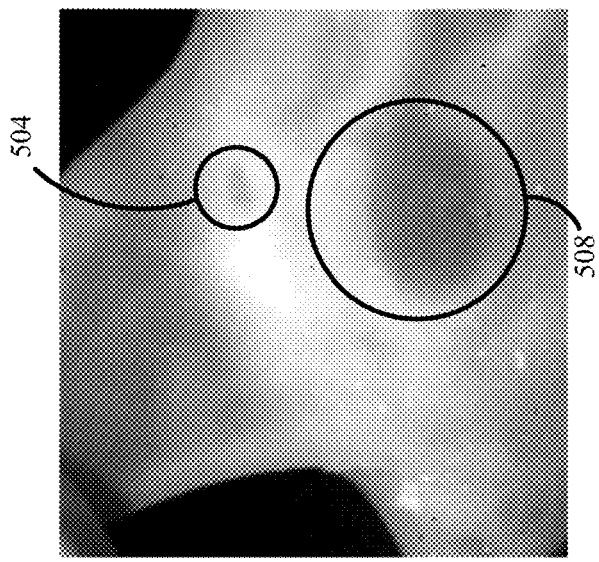
FIG. 8B shows an image of the region of the mouse of FIG. 8A taken using an imaging system before an adjuvant is injected.
Figure 8C:
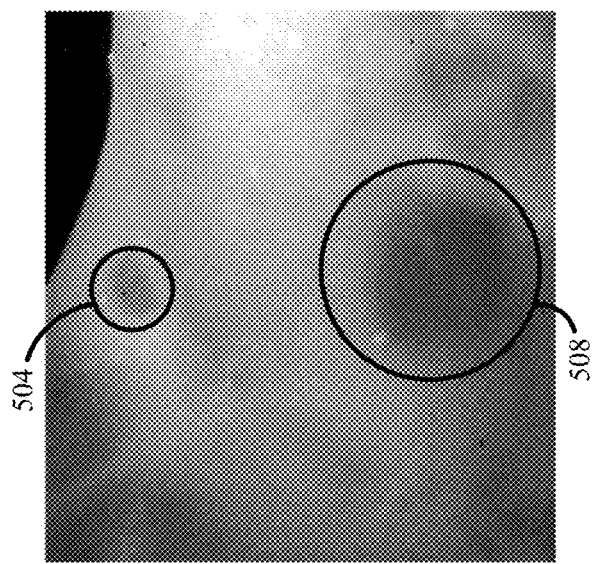
FIG. 8C shows an image of the region of the mouse of FIG. 8A taken using the imaging system forty-eight hours after the adjuvant is injected.

FIGS. 8A-C shows exemplary imaging results of mice. The imaging system used includes an LED emitting around 1200 nm light as a light source and a liquid nitrogen cooled InGaAs camera as a sensor. FIG. 8A shows an image of a region of a mouse taken with a standard camera. FIG. 8B shows an image of the region of the mouse taken using the imaging system before an adjuvant is injected. A lymph node 504 and a bladder 508 can be visualized. FIG. 8C shows an image of the region of the mouse taken using the imaging system forty-eight hours after the adjuvant is injected. The lymph node 504 and the bladder 508 can be visualized. The results show the lymph node 504 has significantly grown in size in the forty-eight hour period after the adjuvant is injected.

Figure 9C:
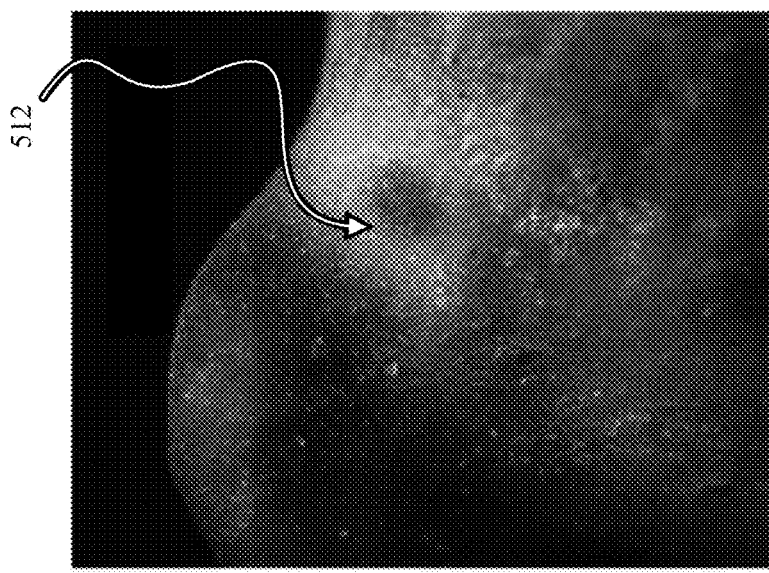
FIG. 9C shows an image of the region of the mouse of FIG. 9A taken using the imaging system forty-eight hours after the adjuvant is injected.
Figure 9B:
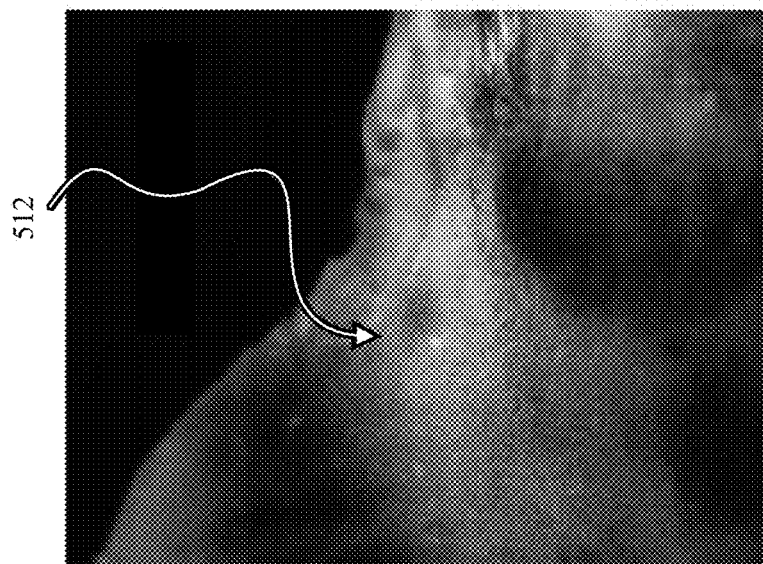
FIG. 9B shows an image of the region of the mouse of FIG. 9A taken using an imaging system before an adjuvant is injected.
Figure 9A:
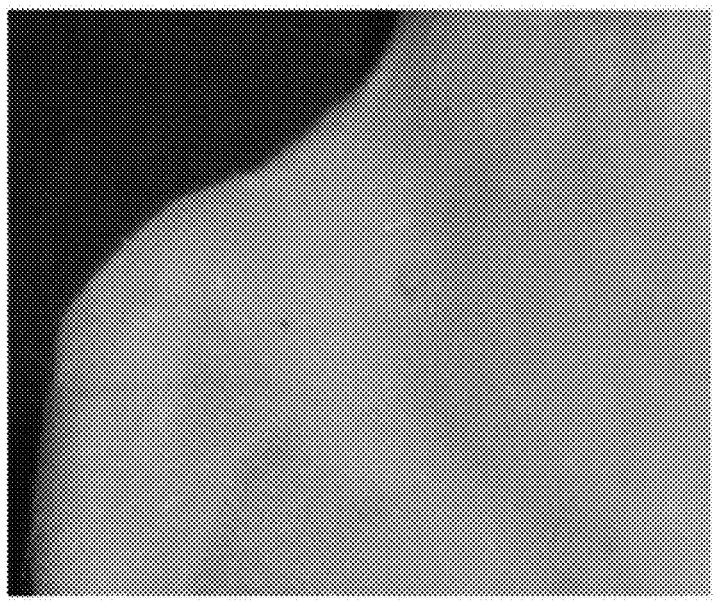
FIG. 9A shows an image of a region of a mouse taken with a standard camera.

FIGS. 9A-C shows exemplary imaging results of mice. The imaging system used includes a halogen lamp as a light source with longpass filters to filter light from the lamp, and a standard silicon camera as a sensor, similar to the imaging system 200 in FIG. 2. FIG. 9A shows an image of a region of a mouse taken with a standard camera. FIG. 9B shows an image of the region of the mouse taken using the imaging system before an adjuvant is injected. FIG. 9C shows an image of the region of the mouse taken using the imaging system forty-eight hours after the adjuvant is injected. The results show the lymph nodes, such as lymph node 512, have significantly grown in size in the forty-eight hour period after the adjuvant is injected. The results are similar in quality to more expensive systems such as the imaging system 100 shown in FIG. 1. Furthermore, the imaging system used to generate FIGS. 9B-C is more compatible with ambient light than other imaging systems.

FIGS. 10A-10E show imaging results of a lymph node using various illumination wavelengths and an InGaAs camera. FIG. 10A was taken when an illumination wavelength of 1000 nm was used. FIG. 10B was taken when an illumination wavelength of 1175 nm was used. FIG. 10C was taken when an illumination wavelength of 1250 nm was used. FIG. 10D was taken when an illumination wavelength of 1375 nm was used. FIG. 10E was taken when an illumination wavelength of 1550 nm was used.

FIGS. 11A-M show imaging results of a lymph node in an ex-vivo pig mesenteric tissue sample. The lymph node was imaged using different illumination wavelengths and sensors included in an imaging system in accordance with embodiments of the invention. A single wavelength LED optical source was used to generate illumination wavelengths of 690 nm and 730 nm. A continuous wavelength lamp with a bandpass filter was used generate illumination wavelengths ranging from 810 nm to 1575 nm. A continuous wavelength lamp without a bandpass filter was used to generate the 8-10 μm illumination. The 8-10 μm illumination was achieved because the sensor used was a heat camera only sensitive to 8-10 μm wavelength light. For 690 nm and 730 nm wavelength illumination, a silicon camera was used as the sensor. For illumination wavelengths ranging from 810 nm to 1575 nm, an InGaAs camera was used as the sensor. For all illumination wavelengths, the imaging system included orthogonally positioned polarizers. Each individual illumination wavelength represents the most dominant wavelength in a band of wavelength.

For each illumination wavelength, the signal-to-noise ratio was measured in order to measure the performance of the illumination wavelength. A higher signal-to-noise ratio is preferable because the lymph node will stand out more against surrounding tissue.

Figure 11A:
FIG. 11A shows an image including a lymph node generated using 690 nm wavelength illumination.
Figure 11B:
FIG. 11B shows an image including the lymph node of FIG. 11A of FIG. 11A generated using 730 nm wavelength illumination.
Figure 11C:
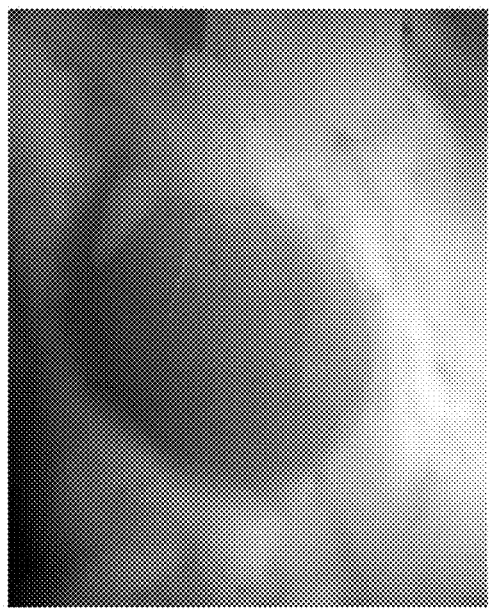
FIG. 11C shows an image including the lymph node of FIG. 11A generated using 810 nm wavelength illumination.
Figure 11D:
FIG. 11D shows an image including the lymph node of FIG. 11A generated using 900-950 nm wavelength illumination.
Figure 11E:
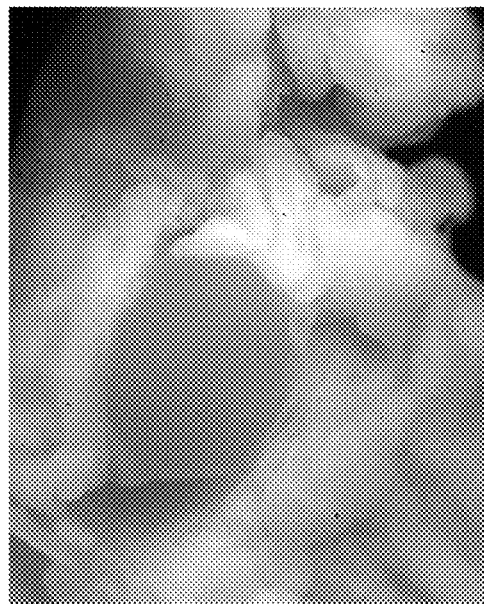
FIG. 11E shows an image including the lymph node of FIG. 11A generated using 1000 nm wavelength illumination.
Figure 11F:
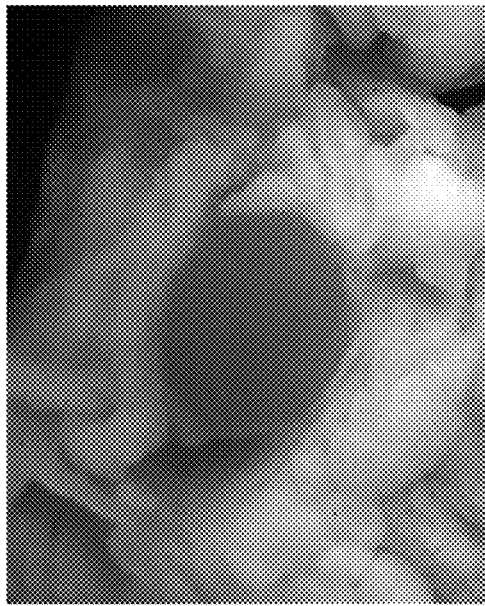
FIG. 11F shows an image including the lymph node of FIG. 11A generated using 1125 nm wavelength illumination.
Figure 11G:
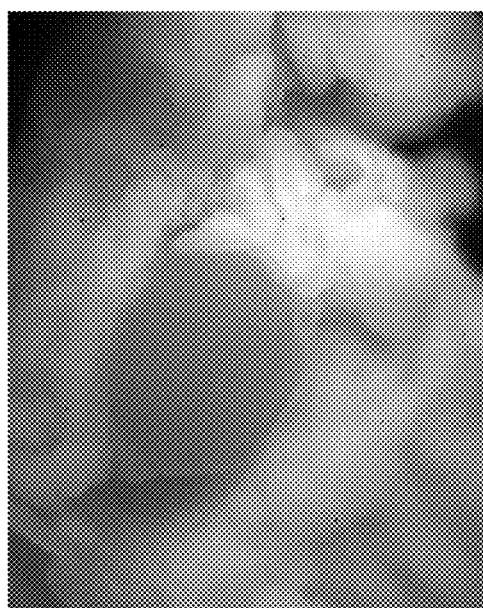
FIG. 11G shows an image including the lymph node of FIG. 11A generated using 1175 nm wavelength illumination.
Figure 11H:
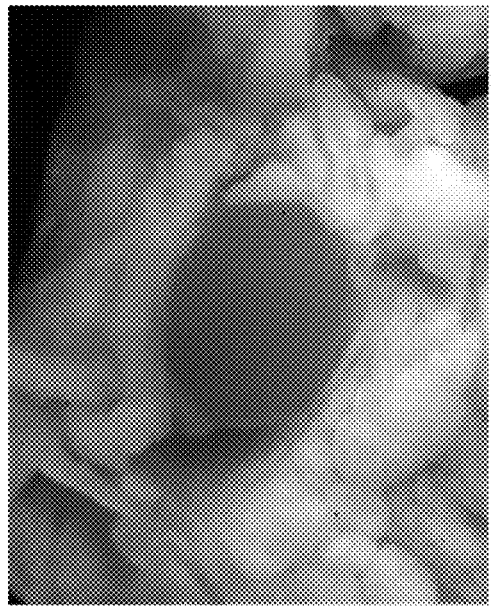
FIG. 11H shows an image including the lymph node of FIG. 11A generated using 1250 nm wavelength illumination.
Figure 11J:
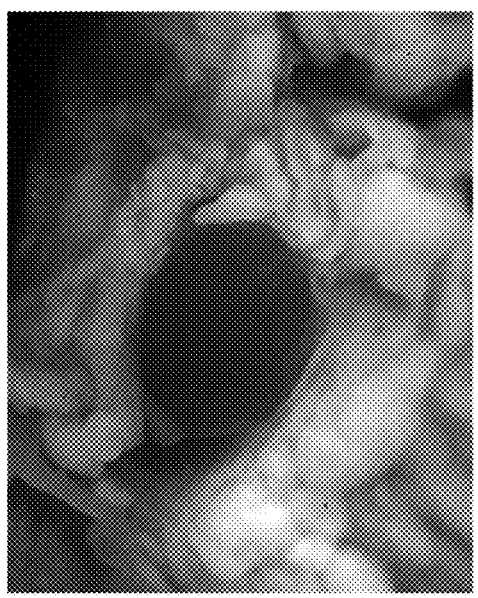
FIG. 11J shows an image including the lymph node of FIG. 11A generated using 1375 nm wavelength illumination.
Figure 11I:
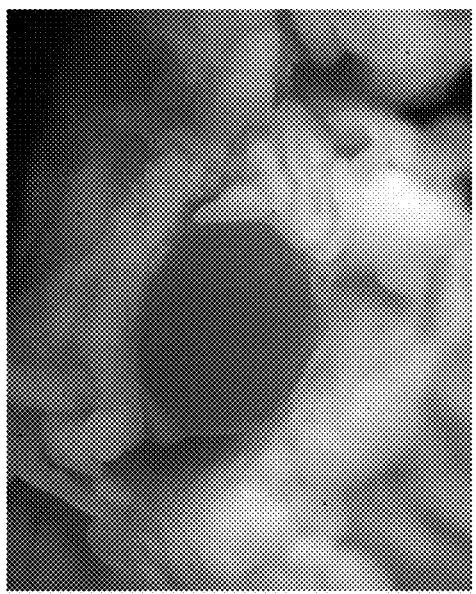
FIG. 11I shows an image including the lymph node of FIG. 11A generated using 1300 nm wavelength illumination.
Figure 11M:
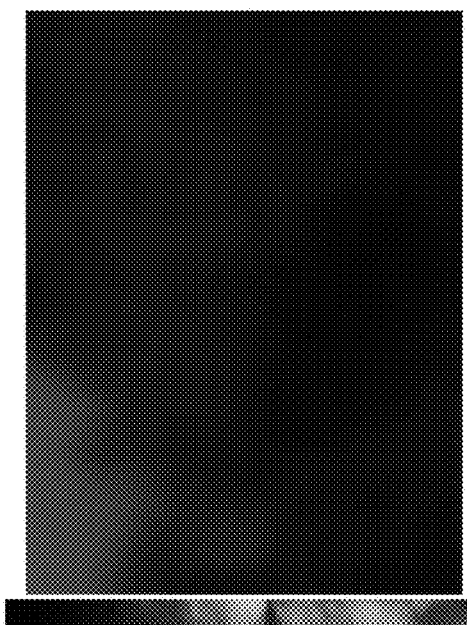
FIG. 11M shows an image including the lymph node of FIG. 11A generated using 8-10 µm wavelength illumination.
Figure 11L:
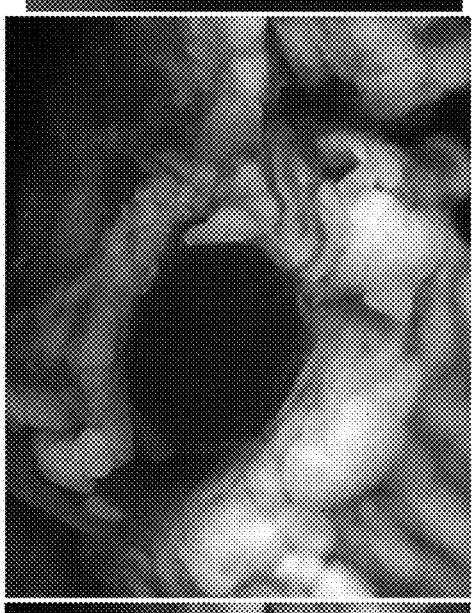
FIG. 11L shows an image including the lymph node of FIG. 11A generated using 1575 nm wavelength illumination.
Figure 11K:
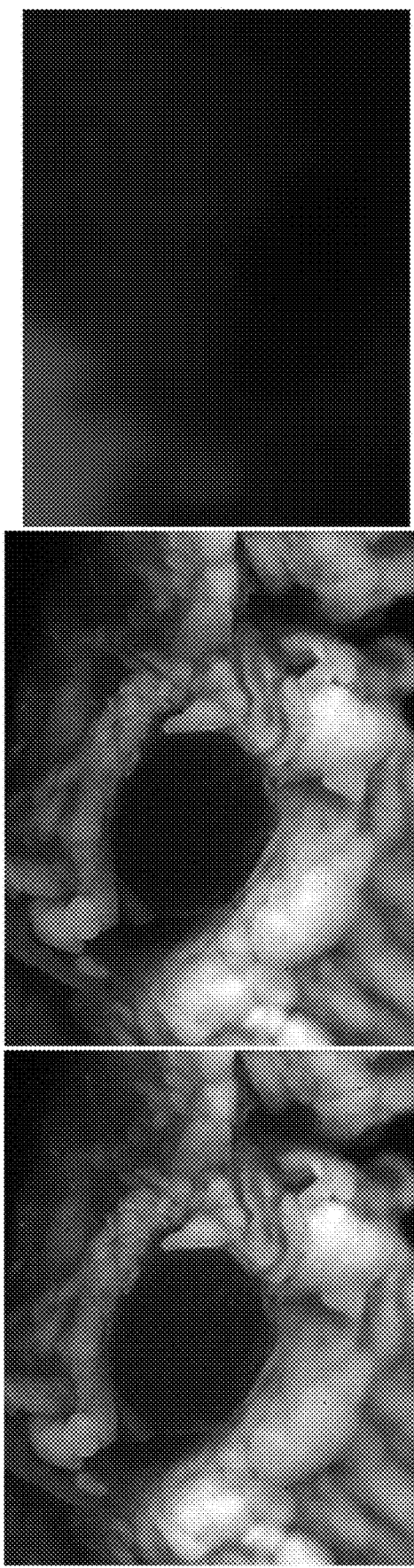
FIG. 11K shows an image including the lymph node of FIG. 11A generated using 1550 nm wavelength illumination.

FIG. 11A shows an image including the lymph node generated using 690 nm wavelength illumination. FIG. 11B shows an image including the lymph node generated using 730 nm wavelength illumination. FIG. 11C shows an image including the lymph node generated using 810 nm wavelength illumination. FIG. 11D shows an image including the lymph node generated using 900-950 nm wavelength illumination. FIG. 11E shows an image including the lymph node generated using 1000 nm wavelength illumination. FIG. 11F shows an image including the lymph node generated using 1125 nm wavelength illumination. FIG. 11G shows an image including the lymph node generated using 1175 nm wavelength illumination. FIG. 11H shows an image including the lymph node generated using 1250 nm wavelength illumination. FIG. 11I shows an image including the lymph node generated using 1300 nm wavelength illumination. FIG. 11J shows an image including the lymph node generated using 1375 nm wavelength illumination. FIG. 11K shows an image including the lymph node generated using 1550 nm wavelength illumination. FIG. 11L shows an image including the lymph node generated using 1575 nm wavelength illumination. FIG. 11M shows an image including the lymph node generated using 8-10 μm wavelength illumination.

Table 1 below summarizes the signal-to-noise ratio for each illumination wavelength. The results in Table 1 show that 1550 illumination wavelength performed the best, with the highest signal-to-noise ratio of 24. Illumination wavelengths ranging from 1175-1375 had comparable performance that provide usable performance. Illumination wavelengths at or below 810 nm had much worse performance than illumination wavelengths ranging from 900-1575 nm. The 8-10 μm wavelength illumination performed significantly worse than the 1550 nm or 1575 nm wavelength illumination, suggesting that illumination wavelengths significantly above 1575 nm may result in decreased performance.

TABLE 1

| Illumination Wavelength | Signal-To-Noise Ratio | Corresponding FIG. |
|---|---|---|
| 690 nm | 4 | 11A |
| 730 nm | 2 | 11B |
| 810 nm | 3 | 11C |
| 900-950 nm | 5 | 11D |
| 1000 nm | 9 | 11E |
| 1125 nm | 8 | 11F |
| 1175 nm | 10 | 11G |
| 1250 nm | 12 | 11H |
| 1300 nm | 11 | 11I |
| 1375 nm | 13 | 11J |
| 1550 nm | 20 | 11K |
| 1575 nm | 24 | 11L |
| 8-10 μm | 8 | 11M |

Figure 12B:
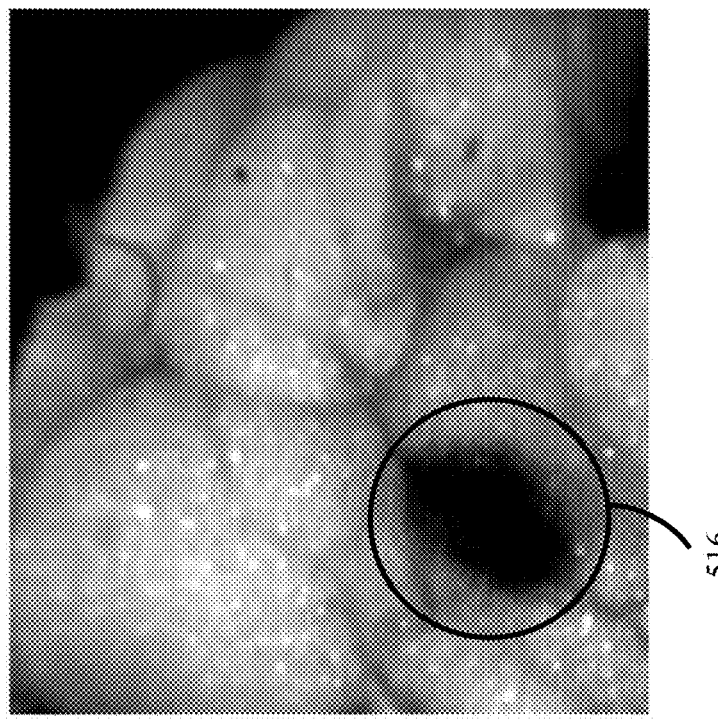
FIG. 12B shows an image of the tissue of FIG. 12A generated using an embodiment of the imaging system of FIG. 3.
Figure 12A:
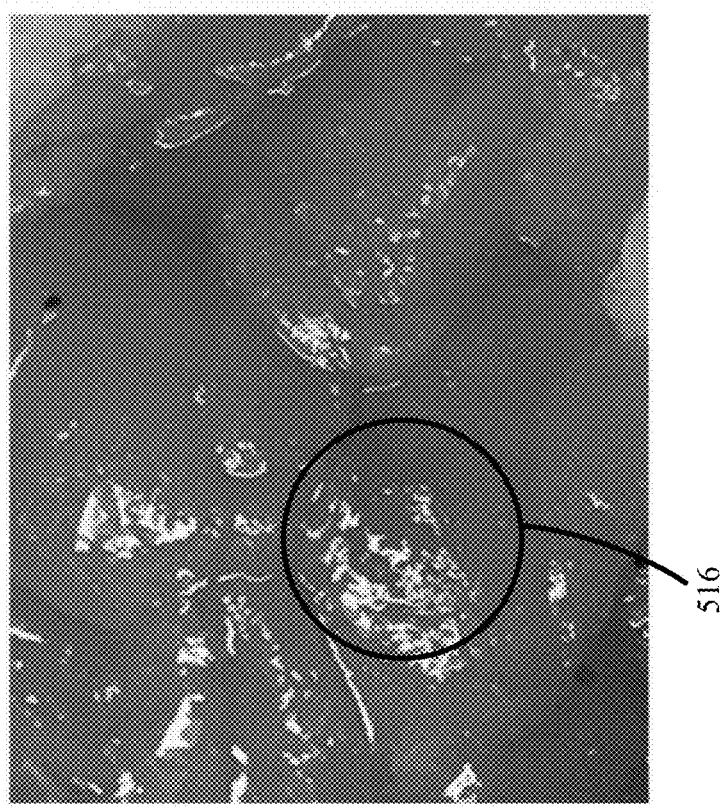
FIG. 12A shows an image of tissue generated using a regular camera and ambient visible light.

Referring now to FIG. 12A and FIG. 12B, a comparison of images of a lymph node 516 in an ex-vivo human tissue sample generated using different imaging techniques is shown. FIG. 12A shows an image of the lymph node 516 generated using a regular camera and ambient visible light. FIG. 12B shows an image of the lymph node 516 generated using an embodiment of the imaging system 300 of FIG. 3. The lymph node 516 is much more clearly visualized in FIG. 12B.

This disclosure provides various embodiments of imaging systems that each provide a set of advantages over other imaging systems. One advantage is that the imaging systems are entirely non-invasive and label-free. This advantage makes the provided imaging systems stand out against the commonly used techniques based on methylene blue, Indocyanine green, and other injected dyes. The imaging systems do not require injection or operation (e.g., a cutting operation) to achieve high imaging contrast of the lymph nodes. It is also noted that the lymph nodes are in vivo when imaged by the imaging system, in contrast to other imaging systems that require lymph nodes and/or surrounding tissue to be removed from a subject in order to perform imaging of the lymph nodes.

Another advantage of the imaging systems provided herein is the increased safety compared to other imaging modalities. The systems only use infrared light at very low intensity. Images shown in the figures listed in this document were taken with only 1 mW optical power illumination, which is thousands of times lower than the exposure limit imposed by regulations. This advantage makes the disclosed imaging systems stand out against CT, PET, and others that inherently pose health hazards to patients. This disclosure describes an optical method for visualizing lymph nodes conveniently without any injection. The method uses illumination light between 800-1700 nm and sensors that are able to detect this wavelength range or part of this wavelength range. The imaging systems can utilize the illumination light to detect lymph nodes using the inherent absorption spectrum of lymph nodes. Using illumination light between 800-1700 nm in wavelength, and especially 1550 nm in wavelength, the imaging system generates images showing lymph nodes that naturally stand out from their surrounding tissues including fat, blood, and/or hemorrhages as described above. Image contrast of lymph nodes can be improved by the implementation of polarizers; however, they are not necessary for the method. This disclosure provides systems and methods to visualize lymph nodes noninvasively and can become a powerful tool for health screening, disease prevention, diagnosis, and treatment.

Certain embodiments of imaging systems provided by the disclosure can also be economically constructed. For example, embodiments similar to the imaging system 200 of FIG. 2 may cost less than 100 dollars to build. Thus, certain lymph node imaging systems can be constructed far more affordably than any of the cross-sectional imaging modalities. CT, MRI, Ultrasound and PET instruments cost from tens of thousands of US dollars to millions of US dollars. The affordability of these provided imaging systems will help make a far larger impact in clinical settings. These imaging systems can be potentially used by medical practitioners or even regular consumers to conduct routine health checks, track disease reoccurrence, etc. Also, unlike the cross-sectional modalities, the wavelength range of the disclosed imaging systems are specific to natural lymph nodes and lymphatic vessels, (i.e. lymph nodes and lymphatic vessels without any external injections). Even imaging systems that include relatively more expensive components (e.g., an InGaAs camera used as the sensor) may still be constructed more economically than at least some of the cross-sectional modalities mentioned above.

It should be understood that the above described steps of the processes of FIG. 6 can be executed or performed in an order or sequence not limited to the order and sequence shown and described in the figures. Also, some of the above steps of the processes of FIGS. 5 and 6 can be executed or performed substantially simultaneously where appropriate or in parallel to reduce latency and processing times.

In some embodiments, aspects of the present disclosure, including computerized implementations of methods, can be implemented as a system, method, apparatus, or article of manufacture using standard programming or engineering techniques to produce software, which can be firmware, hardware, or any combination thereof to control a processor device, a computer (e.g., a processor device operatively coupled to a memory), or another electronically operated controller to implement aspects detailed herein. Accordingly, for example, embodiments of the invention can be implemented as a set of instructions, tangibly embodied on a non-transitory computer-readable media, such that a processor device can implement the instructions based upon reading the instructions from the computer-readable media. Some embodiments of the invention can include (or utilize) a device such as an automation device, a special purpose or general purpose computer including various computer hardware, software, firmware, and so on, consistent with the discussion below.

The term "article of manufacture" as used herein is intended to encompass a computer program accessible from any computer-readable device, carrier (e.g., non-transitory signals), or media (e.g., non-transitory media). For example, computer-readable media can include but can be not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick, and so on). Additionally, it should be appreciated that a carrier wave can be employed to carry computer-readable electronic data such as those used in transmitting and receiving electronic mail or in accessing a network such as the Internet or a local area network (LAN). Those skilled in the art will recognize many modifications may be made to these configurations without departing from the scope or spirit of the claimed subject matter.

Certain operations of methods according to the invention, or of systems executing those methods, may be represented schematically in the Figures or otherwise discussed herein. Unless otherwise specified or limited, representation in the Figures of particular operations in particular spatial order may not necessarily require those operations to be executed in a particular sequence corresponding to the particular spatial order. Correspondingly, certain operations represented in the Figures, or otherwise disclosed herein, can be executed in different orders than can be expressly illustrated or described, as appropriate for particular embodiments of the invention. Further, in some embodiments, certain operations can be executed in parallel, including by dedicated parallel processing devices, or separate computing devices configured to interoperate as part of a large system.

As used herein in the context of computer implementation, unless otherwise specified or limited, the terms "component," "system," "module," etc. can be intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

As used herein, the term, "controller" and "processor" include any device capable of executing a computer program, or any device that can include logic gates configured to execute the described functionality. For example, this may include a processor, a microcontroller, a field-programmable gate array, a programmable logic controller, etc.

The discussion herein is presented for a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention can be not intended to be limited to embodiments shown, but can be to be accorded the widest scope consistent with the principles and features disclosed herein. The detailed description is to be read with reference to the figures, in which like elements in different figures have like reference numerals. The figures, which can be not necessarily to scale, depict selected embodiments and can be not intended to limit the scope of embodiments of the invention. Skilled artisans will recognize the examples provided herein have many useful alternatives and fall within the scope of embodiments of the invention.

Thus, as described above, systems and methods are provided to visualize lymphatic components with near-infrared (800-1400 nm) and/or short-wave infrared (1400-3000 nm). For example, illumination between 800-1700 nm may be used. For some applications, an illumination wavelength between 1500-1600 nm such as 1550 nm may beneficial for imaging lymphatic components. In one embodiment, only 1550 nm wavelength illumination may be used.

The systems and methods described herein provide near-infrared and/or short-infrared imaging techniques that use one or multiple near-infrared or short-wave infrared light sources and sensors. The imaging system can work together with polarizers. A polarizer can be placed in front of the light source(s), which may also be referred to as optical source(s), and another polarizer can be placed in front of the sensor(s). The rotational angle of between two polarizers can be adjusted to minimize direct reflection off the skin of a human or animal and optimize the visualization of lymphatic components. In some configurations, the use of a polarizer in front of the light source(s) can be unnecessary, and the imaging system can function without the polarizer positioned in front of the light source(s). Some light sources emit linearly polarized light due to its inherent working mechanism without a polarizer. Thus, polarizers are helpful for improving the contrast of lymphatic components; however, they are not necessary. Lymphatic components can still be visualized without any polarizers or polarization modifications, particularly when the illumination wavelength is between 800-1700 nm, and the sensor is ready to detect light in this wavelength range.

In one aspect, the present disclosure provides a lymphatic component imaging system. The system includes an optical source configured to provide infrared illumination to a region of a subject having at least one lymphatic component, a sensor configured to sense a reflected portion of the infrared illumination directly reflected from the region, and a controller in communication with the optical source and the sensor and configured to cause the optical source to provide the infrared illumination to the region, receive, from the sensor, information corresponding to the reflected portion of the infrared illumination, and generate at least one image indicative of the at least one lymphatic component in the subject using the information.

The system may be configured to generate the at least one image indicative of the at least one lymphatic component without reference light. The system may be configured to generate the at least one image indicative of the at least one lymphatic component without information from ambient light surrounding the sensor. In the system, the optical source may include a laser. In the system, the optical source may include a light emitting diode. The system may further include a longpass or bandpass filter arranged between the region and the optical source and having with a cutoff wavelength of no less than 800 nm. In the system, the sensor may include at least one of a silicon camera, an InGaAs camera, and a black silicon camera. The system may further include a polarizer arranged between the region and the sensor. The system may not include a contrast agent and the at least one lymphatic component may include a lymph node or a lymphatic vessel. In the system, the infrared illumination may have an illumination wavelength of 800-1700 nm.

In another aspect, the present disclosure provides a method for imaging lymphatic components without a contrast agent. The method includes providing, using an optical source, an infrared illumination to an in vivo region of a subject having lymphatic components, detecting a reflected portion of the infrared illumination directly reflected from the region using a sensor positioned thereabout, and generating at least one image indicative of the lymphatic components in the subject using the reflected portion of the infrared illumination.

In the method, the infrared illumination may have an illumination wavelength of 800-2000 nm. In the method, the infrared illumination may be provided without use of a polarizer. The method may further include rotating a polarizer in front of the sensor until a lowest overall intensity is detected by the sensor. In the method, the infrared illumination may have an optical power of no more than 1 mW. The method may further include positioning a polarizer between the region and the sensor, and arranging the polarizer to be approximately orthogonal to the infrared illumination directly reflected from the region. The method may further include adjusting at least one of the polarizer and the light source until a threshold contrast level is achieved at the sensor.

In yet another aspect, the present disclosure provides a method for imaging lymphatic components without a mirror. The method includes providing, using an optical source, an infrared illumination to a region of a subject having lymphatic components, detecting a reflected portion of the infrared illumination directly reflected from the region using a sensor positioned thereabout, and generating at least one image indicative of the lymphatic components in the subject using the reflected portion of the infrared illumination. In the method, the infrared illumination may have an illumination wavelength of 800-2000 nm. In the method, the infrared illumination may be provided without use of a polarizer.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A system for imaging a lymphatic component, the system comprising:
   an optical source configured to provide infrared illumination having a polarization to a region of a subject having at least one lymphatic component, wherein the infrared illumination has an illumination wavelength of 1000-2600 nm;
   a sensor configured to sense a reflected portion of the infrared illumination having an opposite polarization to that of the polarization of illumination directly reflected from the region; and
   a controller in communication with the sensor and configured to:
      receive, from the sensor, information corresponding to the reflected portion of the infrared illumination;
      generate at least one image indicative of the at least one lymphatic component in the subject using the information; and
      output the at least one image to at least one of a display and/or a memory.

2. The system of claim 1, wherein the controller is configured to generate the at least one image indicative of the at least one lymphatic component without reference light.

3. The system of claim 1, wherein the controller is configured to generate the at least one image indicative of the at least one lymphatic component without information from ambient light surrounding the sensor.

4. The system of claim 1, wherein the optical source includes a laser.

5. The system of claim 1, wherein the optical source includes a light emitting diode.

6. The system of claim 1, further comprising a longpass or bandpass filter arranged between the region and the optical source and having a cutoff wavelength of no less than 800 nm.

7. The system of claim 1, wherein the sensor includes at least one of a silicon camera, an InGaAs camera, or a black silicon camera.

8. The system of claim 1, wherein the sensor includes at least one of a germanium camera, a germanium-tin on silicon camera, a quantum dot shortwave infrared camera, or a mercury-cadmium-telluride camera.

9. The system of claim 1, further comprising a polarizer arranged between the region and the sensor.

10. The system of claim 1, wherein the at least one lymphatic component is free of a contrast agent and includes at least one of a lymph node or a lymphatic vessel.

11. The system of claim 1, wherein the infrared illumination has an illumination wavelength of 1000-1700 nm.

12. The system of claim 1, wherein the infrared illumination has an illumination wavelength of 1500-1700 nm.

13. A method for imaging lymph nodes or lymphatic vessels in vivo without a contrast agent, the method comprising:
providing, using an optical source, an infrared illumination having a polarization to an in vivo region of a subject having lymph nodes or lymphatic vessels that are free of a contrast agent;
detecting a reflected portion of the infrared illumination directly reflected from the region and having a opposite polarization to the polarization using a sensor positioned to receive the illumination directly reflected from the region;
generating at least one image indicative of the lymph nodes or lymphatic vessels that are free of a contrast agent in the subject using the reflected portion of the infrared illuminations; and
rotating a polarizer in front of the sensor until a lowest overall intensity is detected by the sensor.

14. The method of claim 13, wherein the infrared illumination has an illumination wavelength of 800-2000 nm.

15. The method of claim 14, wherein the infrared illumination is provided without use of a polarizer.

16. The method of claim 13, wherein the infrared illumination has an optical power of no more than 1 mW.

17. The method of claim 13 further comprising:
positioning a polarizer between the region and the sensor; and
arranging the polarizer to be approximately orthogonal to the infrared illumination directly reflected from the region.

18. The method of claim 17 further comprising adjusting at least one of the polarizer and the light source until a threshold contrast level is achieved at the sensor.

19. A method for imaging lymph nodes or lymphatic vessels without a mirror, the method comprising:
providing, using an optical source, an infrared illumination to a region of a subject having lymph nodes or lymphatic vessels, wherein the infrared illumination has an illumination wavelength of 1000-2600 nm;
detecting a reflected portion of the infrared illumination directly reflected from the region using a sensor positioned to receive the illumination directly reflected from the region; and
generating at least one image indicative of the lymph nodes or lymphatic vessels in the subject using the reflected portion of the infrared illumination.

20. The method of claim 19, wherein the infrared illumination has an illumination wavelength of 1000-2000 nm.

21. The method of claim 20, wherein the infrared illumination is provided without use of a polarizer.

22. A system for imaging a lymphatic component, the system comprising:
an optical source configured to provide infrared illumination having a polarization to a region of a subject having at least one lymphatic component, wherein the infrared illumination has an illumination wavelength of 1000-2600 nm,
a sensor configured to:
sense a reflected portion of the infrared illumination having an opposite polarization to that of the polarization directly reflected from the region;
generate at least one image indicative of the at least one lymphatic component in the subject based on the reflected portion of the infrared illumination; and
output the at least one image to at least one of an external display or an external memory.

23. A system for imaging a lymphatic component, the system comprising:
an optical source configured to provide infrared illumination having a polarization to a region of a subject having at least one lymphatic component;
a sensor configured to sense a reflected portion of the infrared illumination having an opposite polarization to that of the polarization of illumination directly reflected from the region;
a controller in communication with the sensor and configured to:
receive, from the sensor, information corresponding to the reflected portion of the infrared illumination;
generate at least one image indicative of the at least one lymphatic component in the subject using the information; and
output the at least one image to at least one of a display and/or a memory; and
a longpass or bandpass filter arranged between the region and the optical source and having a cutoff wavelength of no less than 800 nm.

24. The system of claim 23, wherein the controller is configured to generate the at least one image indicative of the at least one lymphatic component without reference light.

25. The system of claim 23, wherein the controller is configured to generate the at least one image indicative of the at least one lymphatic component without information from ambient light surrounding the sensor.

26. The system of claim 23, wherein the optical source includes a laser.

27. The system of claim 23, wherein the optical source includes a light emitting diode.

28. The system of claim 23, wherein the sensor includes at least one of a silicon camera, an InGaAs camera, or a black silicon camera.

29. The system of claim 23, wherein the sensor includes at least one of a germanium camera, a germanium-tin on silicon camera, a quantum dot shortwave infrared camera, or a mercury-cadmium-telluride camera.

30. The system of claim 23, further comprising a polarizer arranged between the region and the sensor.

31. The system of claim 23, wherein the at least one lymphatic component is free of a contrast agent and includes at least one of a lymph node or a lymphatic vessel.

32. The system of claim 23, wherein the infrared illumination has an illumination wavelength of 1000-2600 nm.

33. The system of claim 32, wherein the infrared illumination has an illumination wavelength of 1000-1700 nm.

34. The system of claim 33, wherein the infrared illumination has an illumination wavelength of 1500-1700 nm.

35. A method for imaging lymph nodes or lymphatic vessels in vivo without a contrast agent, the method comprising:
providing, using an optical source, an infrared illumination having a polarization to an in vivo region of a subject having lymph nodes or lymphatic vessels that are free of a contrast agent, wherein the infrared illumination has an optical power of no more than 1 mW;
detecting a reflected portion of the infrared illumination directly reflected from the region and having a opposite polarization to the polarization using a sensor positioned to receive the illumination directly reflected from the region; and
generating at least one image indicative of the lymph nodes or lymphatic vessels that are free of a contrast agent in the subject using the reflected portion of the infrared illumination.

36. The method of claim 35, wherein the infrared illumination has an illumination wavelength of 800-2000 nm.

37. The method of claim 36, wherein the infrared illumination is provided without use of a polarizer.

38. The method of claim 35, further comprising rotating a polarizer in front of the sensor until a lowest overall intensity is detected by the sensor.

39. The method of claim 35, further comprising:
positioning a polarizer between the region and the sensor; and
arranging the polarizer to be approximately orthogonal to the infrared illumination directly reflected from the region.

40. The method of claim 35, further comprising adjusting at least one of the polarizer and the light source until a threshold contrast level is achieved at the sensor.

41. The method of claim 13, wherein the infrared illumination has an illumination wavelength of 1000-2600 nm.

42. The method of claim 13, wherein the infrared illumination has an illumination wavelength of 1000-1700 nm.

43. The method of claim 13, wherein the infrared illumination has an illumination wavelength of 1500-1700 nm.

44. The method of claim 19, wherein the infrared illumination has an illumination wavelength of 1000-1700 nm.

45. The method of claim 19, wherein the infrared illumination has an illumination wavelength of 1500-1700 nm.

46. The system of claim 22, wherein the infrared illumination has an illumination wavelength of 1000-1700 nm.

47. The system of claim 22, wherein the infrared illumination has an illumination wavelength of 1500-1700 nm.

48. A method for imaging lymph nodes or lymphatic vessels in vivo without a contrast agent, the method comprising:
providing, using an optical source, an infrared illumination having a polarization to an in vivo region of a subject having lymph nodes or lymphatic vessels that are free of a contrast agent, wherein the infrared illumination has an illumination wavelength of 1000-2600 nm;
detecting a reflected portion of the infrared illumination directly reflected from the region and having a opposite polarization to the polarization using a sensor positioned to receive the illumination directly reflected from the region; and
generating at least one image indicative of the lymph nodes or lymphatic vessels that are free of a contrast agent in the subject using the reflected portion of the infrared illumination.

49. The method of claim 48, wherein the infrared illumination is provided without use of a polarizer.

50. The method of claim 48, further comprising rotating a polarizer in front of the sensor until a lowest overall intensity is detected by the sensor.

51. The method of claim 48, wherein the infrared illumination has an optical power of no more than 1 mW.

* * * * *

UNITED STATES PATENT AND TRADEMARK OFFICE
CERTIFICATE OF CORRECTION

| | | |
|---|---|---|
| PATENT NO. | : 11,576,608 B2 | Page 1 of 1 |
| APPLICATION NO. | : 16/781338 | |
| DATED | : February 14, 2023 | |
| INVENTOR(S) | : Zhongming Li et al. | |

It is certified that error appears in the above-identified patent and that said Letters Patent is hereby corrected as shown below:

In the Specification

Column 1, Line 59, "MM" should be --MRI--.

Column 6, Line 2, "polanizer" should be --polarizer--.

In the Claims

Claim 13, Column 25, Line 33, "illuminations" should be --illumination--.

Signed and Sealed this
Twentieth Day of May, 2025

Coke Morgan Stewart
*Acting Director of the United States Patent and Trademark Office*